United States Patent
Margolin et al.

(10) Patent No.: US 11,077,238 B2
(45) Date of Patent: Aug. 3, 2021

(54) COMPOSITIONS, METHODS, AND DEVICES FOR DIALYSIS

(71) Applicant: Allena Pharmaceuticals, Inc., Newton, MA (US)

(72) Inventors: Alexey Margolin, Newton, MA (US); Danica Grujic, Boston, MA (US); Stefan Pierzynowski, Trelleborg (SE)

(73) Assignee: Allena Pharmaceuticals, Inc., Newton, MA (US)

( * ) Notice: Subject to any disclaimer, the term of this patent is extended or adjusted under 35 U.S.C. 154(b) by 1111 days.

(21) Appl. No.: 14/896,273

(22) PCT Filed: Jun. 6, 2014

(86) PCT No.: PCT/US2014/041318
§ 371 (c)(1),
(2) Date: Dec. 4, 2015

(87) PCT Pub. No.: WO2014/197806
PCT Pub. Date: Dec. 11, 2014

(65) Prior Publication Data
US 2016/0144094 A1  May 26, 2016

Related U.S. Application Data

(60) Provisional application No. 61/832,235, filed on Jun. 7, 2013.

(51) Int. Cl.
| | | |
|---|---|---|
| *A61M 1/28* | (2006.01) | |
| *A61K 38/44* | (2006.01) | |
| *A01K 67/00* | (2006.01) | |
| *A61K 38/43* | (2006.01) | |
| *A61K 38/45* | (2006.01) | |
| *A61K 38/50* | (2006.01) | |
| *A61K 38/51* | (2006.01) | |

(52) U.S. Cl.
CPC ............ *A61M 1/287* (2013.01); *A01K 67/00* (2013.01); *A61K 38/43* (2013.01); *A61K 38/44* (2013.01); *A61K 38/45* (2013.01); *A61K 38/50* (2013.01); *A61K 38/51* (2013.01); *C12Y 101/00* (2013.01); *C12Y 103/03005* (2013.01); *C12Y 114/16001* (2013.01); *C12Y 305/01005* (2013.01); *C12Y 401/01002* (2013.01); *C12Y 403/01024* (2013.01); *A01K 2207/20* (2013.01); *A01K 2227/108* (2013.01); *A01K 2267/03* (2013.01)

(58) Field of Classification Search
None
See application file for complete search history.

(56) References Cited

U.S. PATENT DOCUMENTS

| | | |
|---|---|---|
| 5,039,609 A | 8/1991 | Klein |
| 5,866,778 A | 2/1999 | Hartman et al. |
| 5,976,529 A | 11/1999 | Navia et al. |
| 6,140,475 A | 10/2000 | Margolin et al. |
| 6,218,134 B1 | 4/2001 | Yamauchi et al. |
| 6,229,065 B1 | 5/2001 | Freyssinet et al. |
| 6,235,530 B1 | 5/2001 | Freyssinet et al. |
| 6,281,252 B1 | 8/2001 | Holmes-Farley et al. |
| 6,284,140 B1 * | 9/2001 | Sommermeyer .... A61K 31/715 210/646 |
| 6,503,507 B1 | 1/2003 | Allen |
| 6,541,606 B2 | 4/2003 | Margolin et al. |
| 6,783,965 B1 * | 8/2004 | Sherman ................ A61K 47/60 435/190 |
| 6,929,940 B1 | 8/2005 | Richards et al. |
| 8,012,118 B2 | 9/2011 | Curtin et al. |
| 8,142,775 B2 | 3/2012 | Shenoy et al. |
| 8,431,122 B2 | 4/2013 | Sidhu et al. |
| 8,741,284 B2 | 6/2014 | Shenoy et al. |
| 9,155,785 B2 | 10/2015 | Shenoy et al. |
| 2003/0105424 A1 * | 6/2003 | Karoor ................ A61M 1/1696 604/29 |
| 2003/0113308 A1 | 6/2003 | Sidhu |
| 2003/0198620 A1 | 10/2003 | Ozawa et al. |
| 2004/0229771 A1 | 11/2004 | Deppisch et al. |
| 2004/0234514 A1 | 11/2004 | Sidhu |
| 2005/0123529 A1 * | 6/2005 | O'Loughlin ........... A61K 38/44 424/94.6 |
| 2005/0123539 A1 | 6/2005 | Rusnak |
| 2005/0232901 A1 | 10/2005 | Zaghmout |
| 2006/0104935 A1 | 5/2006 | Margolin et al. |
| 2007/0178070 A1 | 8/2007 | Kaul et al. |
| 2007/0184118 A1 | 8/2007 | Li et al. |

(Continued)

FOREIGN PATENT DOCUMENTS

| | | |
|---|---|---|
| WO | WO 92/02617 A1 | 2/1992 |
| WO | WO-2002/053094 A2 | 7/2002 |

(Continued)

OTHER PUBLICATIONS

Illies et al., Clearance and removal of oxalate in children on intensified dialysis for primary hyperoxaluria type 1, Kidney International (2006) 70, 1642-1648 (Year: 2006).*
Peritoneal Dialysis, What you need to know, Brochure, National Kidney Foundation, 2006 (Year: 2006).*
Harambat et al., Primary Hyperoxaluria, International Journal of Nephrology vol. 2011, Article ID 864580, 11 pages (Year: 2011).*
Campieri et al. (2001) "Reduction of oxaluria after an oral course of lactic acid bacteria at high concentration," Kidney International, 60:1097-1105.
Communication about intention to grant a European patent for European Application 07873799.6, dated Nov. 5, 2012 (5 pages).
Extended European Search Report for European Application 14807765.4, dated Feb. 21, 2017 (14 pages).

(Continued)

*Primary Examiner* — Robert J Yamasaki
(74) *Attorney, Agent, or Firm* — Goodwin Procter LLP

(57) ABSTRACT

Compositions of peritoneal dialysis solutions and metabolizing enzymes, and their uses to treat disorders associated with elevated levels of metabolites are disclosed. Animal models of hyperoxalemia are also disclosed.

9 Claims, 7 Drawing Sheets

(56) References Cited

U.S. PATENT DOCUMENTS

| | | | |
|---|---|---|---|
| 2008/0051696 A1* | 2/2008 | Curtin | A61M 1/1696 604/29 |
| 2008/0311101 A1 | 12/2008 | Shenoy et al. | |
| 2008/0317810 A1* | 12/2008 | Sidhu | C12Y 401/01008 424/423 |
| 2012/0308545 A1 | 12/2012 | Shenoy et al. | |
| 2013/0108607 A1 | 5/2013 | Cowley et al. | |
| 2016/0051647 A1 | 2/2016 | Shenoy et al. | |

FOREIGN PATENT DOCUMENTS

| | | |
|---|---|---|
| WO | WO 2004/018634 A2 | 3/2004 |
| WO | WO 2004/093633 A2 | 11/2004 |
| WO | WO-2009/120707 A1 | 10/2009 |
| WO | WO-2010/115291 A1 | 10/2010 |

OTHER PUBLICATIONS

Hoppe et al. (2004) "Diagnostic and therapeutic strategies in hyperoxaluria: a plea for early intervention," Nephrol. Dial. Transplant., 19(1):39-42.
Office Action for Canadian Patent Application 2659081, dated Dec. 9, 2013 (5 pages).
Office Action for Canadian Patent Application 2659081, dated Apr. 28, 2016 (7 pages).
Office Action for Chinese Patent Application 201310106056.0, dated Mar. 5, 2014 (9 pages).
Office Action for Chinese Patent Application 201310106056.0, dated Aug. 19, 2016 (9 pages).
Rippe et al. (2004) "Fluid and electrolyte transport across the peritoneal membrane during CAPD according to the three-pore model," Perit. Dial. Int., 24(1):10-27.
Zelinski et al. (1997) "Cross-Linked Enzyme Crystals (CLECs): Efficient and Stable Biocatalysts for Preparative Organic Chemistry," Angew. Chem. Int. Ed. Engl., 36(7):722-724.
Anand et al., "Structure of Oxalate Decarboxylase from *Bacillus subtilis* at 1.75 Å Resolution," *Biochemistry*, 41:7659-7669 (2002).
Dashek et al., "Assay and Purification of Enzymes-Oxalate Decarboxylase" Chapter 5 in *Methods in Plant Biochemistry and Molecular Biology*. Boca Raton, FL: CRC Press, 1997: pp. 49-71, with Errata.
Earnest, "Enteric Hyperoxaluria" *Adv. Internal Medicine*, 24:407-427 (1979).
Extended European Search Report issued in European Application No. 07873799.6, dated Mar. 12, 2010 (11 pages).
Gilliland, "A Biological Macromolecule Crystallization Database: A Basis for a Crystallization Strategy" *J. Crystal Growth*, 90:51-59 (1988).
Grujic et al., "Hyperoxaluria Is Reduced and Nephrocalcinosis Prevented with an Oxalate-Degrading Enzyme in Mice with Hyperoxaluria" *Am. J. Nephrol.*, 29(2):86-93 (2009).
Hochgrafe et al. (2007) "S-cysteinylation is a general mechanism for thiol protection of *Bacillus subtilis* proteins after oxidative stress" *J. Biol. Chem.*, 282(36):25981-25985.
International Preliminary Report on Patentability including the Written Opinion dated Feb. 3, 2009 from International PCT Application No. PCT/US2007/75091 (6 pages).
International Search Report and Written Opinion dated Aug. 6, 2008, in International Patent Application No. PCT/US2007/75091, filed Aug. 2, 2007, by Altus Pharmaceuticals Inc. (7 pages).
International Search Report and Written Opinion dated May 7, 2014, in International Patent Application No. PCT/US2014/012008, filed Jan. 17, 2014, by Allena Pharmaceuticals, Inc. (19 pages).
International Search Report and Written Opinion dated Dec. 3, 2014, in International Patent Application No. PCT/US2014/41318, filed Jun. 6, 2014, by Allena Pharmaceuticals, Inc. (4 pages).
Leumann et al., "What is new in primary hyperoxaluria?" *Nephrol. Dial. Transplant.*, 14:2556-2558 (1999).
Leumann et al., "The Primary Hyperoxalurias" *J. Am. Soc. Nephrol.*, 12:1986-1993 (2001).
Magro et al., "Enzymatic oxalate decarboxylation in isolates of *Sclerotinia scleratiorum*" *FEMS Microbiology Letters*, 49:49-52 (1988).
Margolin, "Novel crystalline catalysts" *Trends in Microbiology*, 14:223-230 (1996).
Mcpherson et al., "Crystallization of Macromolecules: General Principles" *Methods Enzymol.*, 114:112-120 (1985).
Monico et al., "Potential mechanisms of marked hyperoxaluria not due to primary hyperoxaluria I or II" *Kidney International*, 62:392-400 (2002).
Parkinson et al., "The determination of plasma oxalate concentrations using an enzyme/bioluminescent assay" *Clin. Chim. Acta*, 152(3):335-345 (1985).
Svedruzić et al., "The enzymes of oxalate metabolism: unexpected structures and mechanisms" *Arch. Biochem. Biophys.*, 433:176-192 (2005).
Tanner et al., "Oxalate Decarboxylase Requires Manganese and Dioxygen for Activity" *J. Biol. Chem.*, 276(47):43627-43634 (2001).
Tanner et al., "*Bacillus subtilis* Yvrk. Is an Acid-Induced Oxalate Decarboxylase" *J. Bacteriol.*, 182(18):5271-5273 (2000).
Vaghjiani et al., "Production and Characterisation of Cross-Linked Enzyme Crystals (CLECs® ) for Application as Process Scale Biocatalysts" 18:151-175 (2000).
Calame, et al. (1995) Nephrol. Dial. Trannsplant., 10: 1212-1217.
Third Party Observations for Application No. EP14807765.4, dated Mar. 16, 2020 (5 pages).

* cited by examiner

Figure 1a. Oxalate levels in serum and peritoneal dialysate from pig infused with 1% sodium oxalate at an infusion rate of 0.2 mL/min
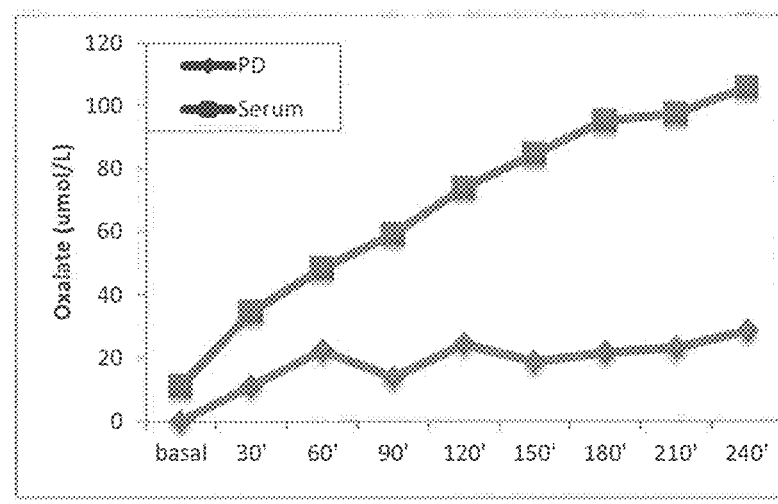
Figure 1b. Oxalate levels in serum and peritoneal dialysate from pig infused with 1 % sodium oxalate at rate 0.35 mL/min
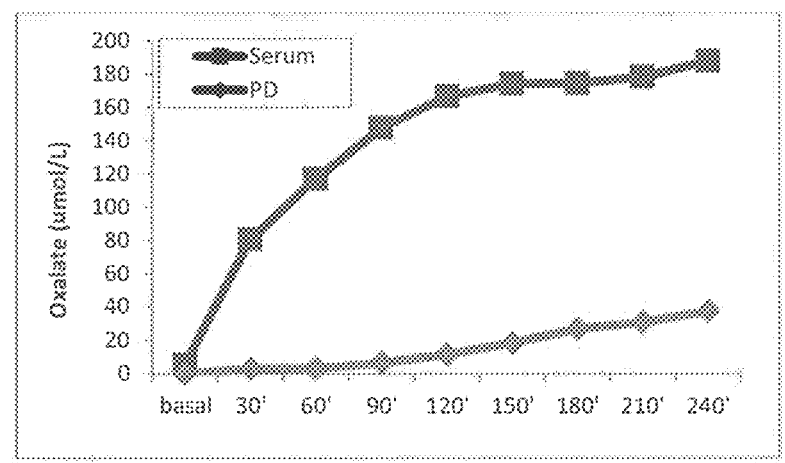

Figure 2. Oxalate concentration in serum and peritoneal dialysate samples from pigs infused with oxalate and administered with PD (control) or PD+OXDC.
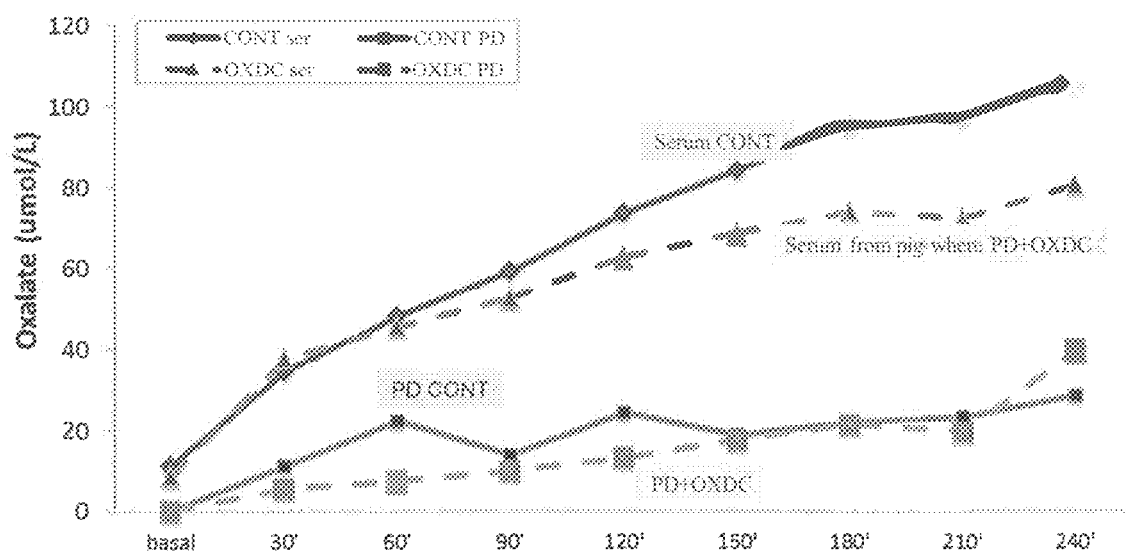

Figure 3. Diagram of an in vitro dialysis model using PD solution GAMBROSOL TRIO™ 10 ± OXDC
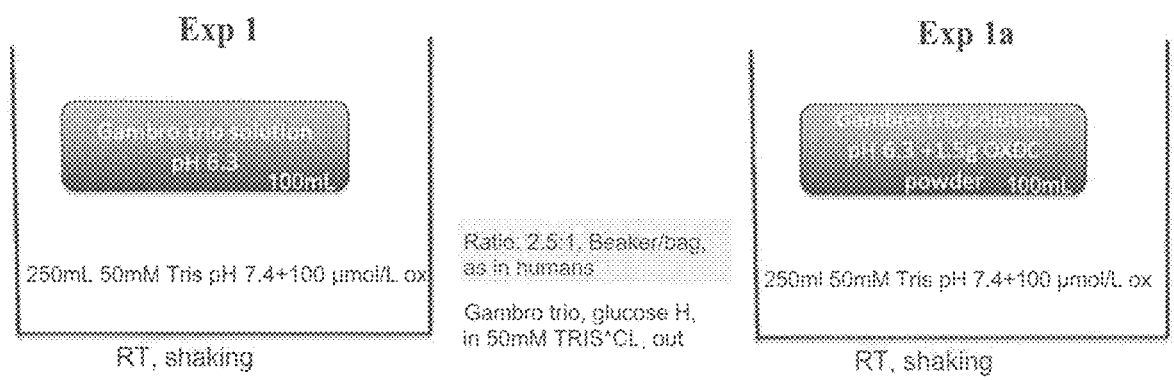

Figure 4. Oxalate concentration in an in vitro dialysis model using GAMBROSOL TRIO™ 10 ± OXDC (15mg/mL).
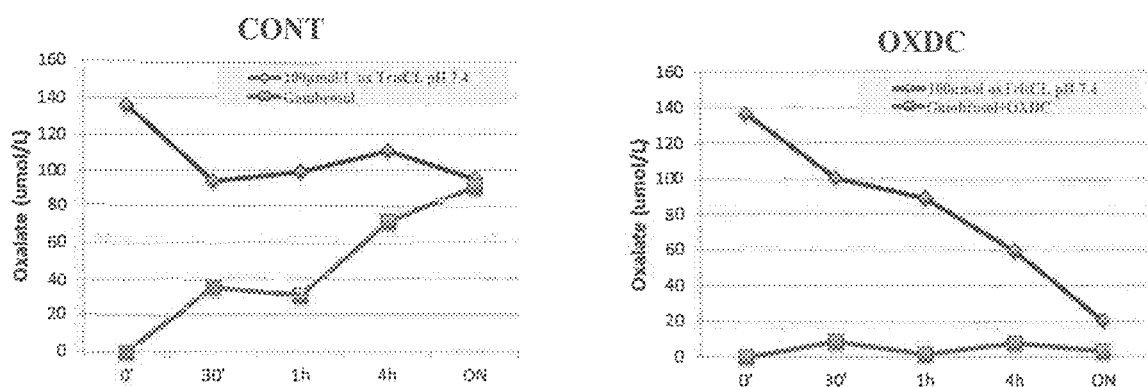

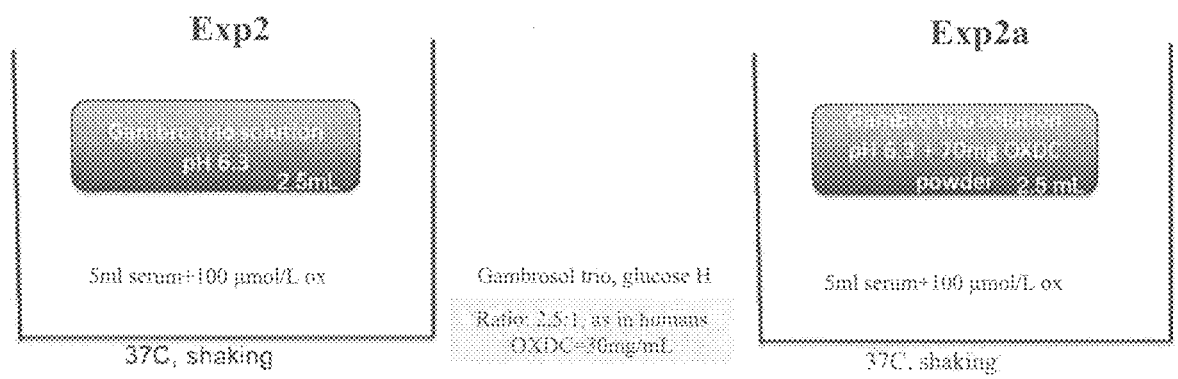
Figure 5. Diagram of an in vitro dialysis model using serum and GAMBROSOL TRIO TM 10 ± OXDC Figure 6. Oxalate concentration in an in vitro dialysis model using serum and GAMBROSOL TRIO™ 10 ± OXDC
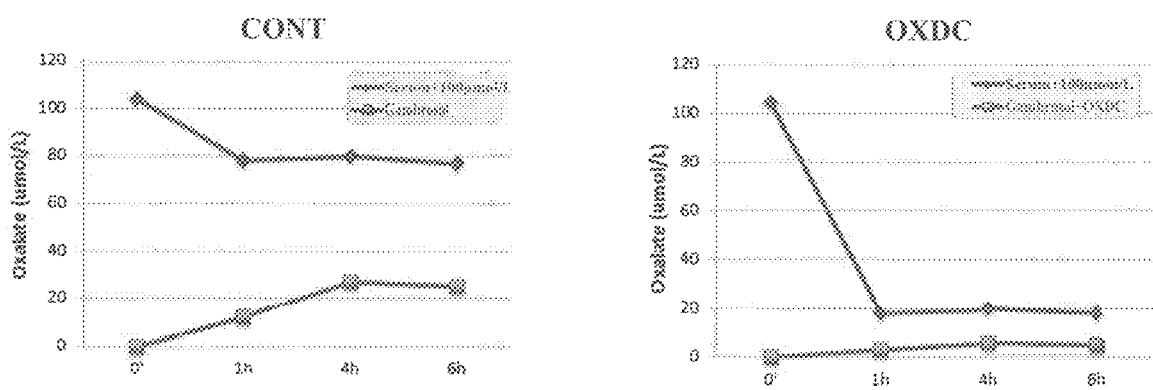

Figure 7. OXDC dosage-dependent reduction of in vitro serum oxalate levels
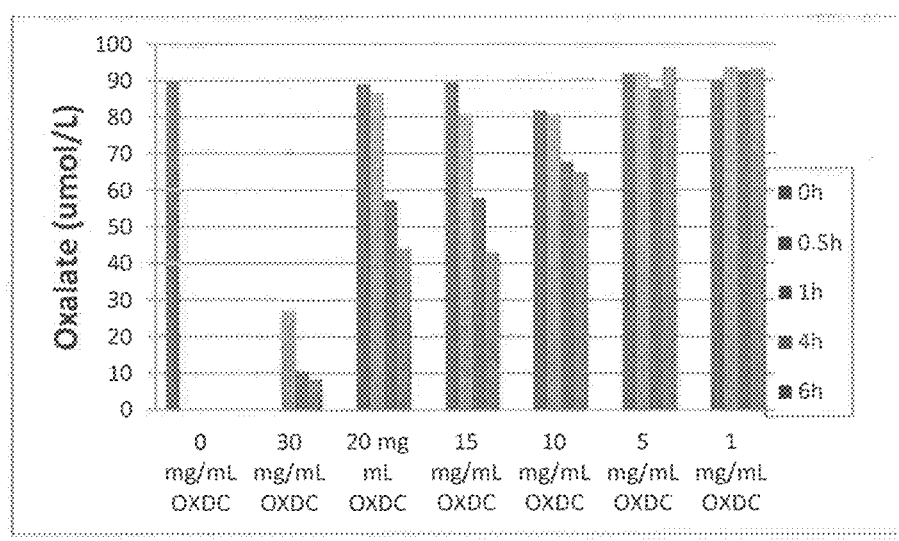

COMPOSITIONS, METHODS, AND DEVICES FOR DIALYSIS

CROSS-REFERENCE TO RELATED APPLICATIONS

This application is a U.S. national stage of International Patent Application PCT/US2014/041318, filed Jun. 6, 2014, which claims the benefit of priority to U.S. Provisional Application No. 61/832,235, filed Jun. 7, 2013, each of which is incorporated herein by reference in its entirety.

BACKGROUND

Oxalic acid is a dicarboxylic acid of the formula $HO_2C-CO_2H$. Oxalic acid exists primarily as oxalate in biological organisms, which is the salt form of oxalic acid. Oxalate is found in foods, such as, e.g., spinach, rhubarb, strawberries, cranberries, nuts, cocoa, chocolate, peanut butter, sorghum, and tea. Oxalate is also a metabolic end product in humans and other mammals. It is excreted by the kidneys into the urine. When combined with calcium, oxalic acid produces an insoluble product, calcium oxalate, which is the most prevalent chemical compound found in kidney stones.

Because mammals do not synthesize enzymes that degrade oxalate, oxalate levels in an individual are normally regulated by filtration and excretion via the kidneys and low absorption of about 5-10% of dietary oxalate along gastrointestinal tracts. Elevated concentrations of oxalate are associated with a variety of pathologies, such as hyperoxalemia, oxalosis, primary hyperoxaluria, enteric hyperoxaluria, idiopathic hyperoxaluria, or end stage renal disease (ESRD). E.g., Hoppe. *Nat. Rev. Nephrol.* 8:467-75 (2012). Increased oxalate can be caused by consuming too much oxalate from foods, by hyperabsorption of oxalate from the intestinal tract, and by abnormalities of endogenous oxalate production. Hyperabsorption of oxalate in the colon and small intestine can be associated with intestinal diseases, including hyperabsorption caused by diseases of bile acid and fat malabsorption; ileal resection; and, for example, by steatorrhea due to celiac disease, exocrine pancreatic insufficiency, intestinal disease, and liver disease.

Hyperoxalemia, or elevation of oxalate in the blood, may be caused, for example, by decreased oxalate excretion in patients with renal failure. Hyperoxalemia may result in precipitation of calcium oxalate in the body tissues or organs named oxalosis. Oxalosis is often associated with hyperoxaluria and includes deposition of calcium oxalate in the kidney tissue (nephrocalcinosis) or urinary tract (e.g., kidney stones, urolithiasis, and nephrolithiasis). Calcium oxalate may also be deposited in, e.g., the eyes, blood vessels, joints, bones, muscles, heart and other major organs, causing damage to the same. See, e.g., Leumann et al., *J. Am. Soc. Nephrol.* 12: 1986 1993 (2001) and Monico et al., *Kidney International* 62:392 400 (2002). The effects of increased oxalate levels can appear in a variety of tissues. For example, deposits in small blood vessels cause painful skin ulcers that do not heal, deposits in bone marrow cause anemia, deposits in bone tissue cause fractures or affect growth in children, and calcium oxalate deposits in the heart cause abnormalities of heart rhythm or poor heart function. Hyperoxaluria often progresses to calcium oxalate stone formation and/or medullar nephrocalcinosis. Such processes may in turn lead to a decline in glomerular filtration rate, elevation in plasma oxalate concentration, and deposition of calcium oxalate crystals in solid organs such as the bones, joints, heart, and retina, which collectively is termed systemic oxalosis. Hoppe et al., *Am. J. Nephrol.* 25:276-281 (2005). Lowering the concentration of oxalate in plasma can prevent the worsening of oxalosis (tissue deposition of oxalate), nephrocalcinosis (interstitial deposition of calcium-oxalate), and calcium oxalate kidney stones in patients with severe primary hyperoxaluria (PH), as well as in patients with end stage renal disease (ERSD). Hoppe, *Nat. Rev. Nephrol.* 8:467-75 (2012); Hoppe et al., *Kidney Int.* 56:268-74 (1999).

Existing methods to treat elevated oxalate levels have not been shown to be effective, and intensive dialysis and organ transplantation may be required in many patients with primary hyperoxaluria, enetric hyperoxaluria, or ESRD. Existing therapies for various hyperoxalurias include high-dose pyridoxine, orthophosphate, magnesium, iron, aluminum, potassium citrate, and cholestyramine treatment, as well as regimes for adjusting diet and fluid intake, for dialysis, and for surgical intervention, such as renal and liver transplantation. In existing methods of peritoneal dialysis, oxalate elimination is not sufficient to remove excessive endogenous production of oxalate, i.e., rate of elimination is slower than the rate of production. Marangella et al., *Contrib. Nephrol.* 136:11-32 (2001). For example, conventional peritoneal dialysis is insufficient to clear adequate quantities of oxalate, especially in patients with systemic oxalosis who have reached ESRD. Cochat et al., *Nephrol. Dial. Transplant.* 27:1279-36 (2012). Therefore, body oxalate accumulation increases rapidly despite intensive dialysis. In addition, patients need constant monitoring to allow for the adjustment of dialysis regimens based on plasma oxalate levels. In fact, it was recognized in the art that no form of dialysis, not even the combination of hemodialysis and peritoneal dialysis, has been able to keep up with the endogenously produced oxalate in hyperoxaluria, let alone to reduce the body oxalate level. Hoppe et al., *Nephrol Dial Transplant.* 19: 39-42 (2004). Hence, patients have had to bear the burden of intensified hemodialysis with five to six sessions of 5 h/week and additionally nightly peritoneal dialysis until kidney transplantation is performed. Hoppe et al., (2004).

For those patients who develop ESRD, management with aggressive (6 or 7 times a week) daily hemodialysis with or without supplemental peritoneal dialysis is merely a temporary remedy, while the patient is awaiting kidney transplantation. However, because the liver is primarily responsible for excessive oxalate production in individuals with primary hyperoxaluria, patients undergoing solely kidney transplantation are often subject to eventual recurrence of renal failure due to progression of oxalate deposits in the new kidney. Combined kidney-liver transplantation or preemptive liver transplantation are the only demonstrated therapeutic modalities for cure in the patient with PH. Hoppe et al., *Pediatr. Nephrol.* 18:986-91 (2003). However, these procedures in and of themselves are associated with significant risk to the patient. Discovery of new therapies to assist in the management of PH until a genetic cure or a cure not involving organ transplantation is identified would help greatly to limit the morbidity and mortality in this patient population.

Accordingly, treatment methods that more effectively reduce a patient's levels of oxalate or other metabolites are needed. More particularly, treatment methods for oxalate or other metabolites buildup in the plasma that is less burdensome than hemodialysis and organ transplantation are urgently needed. There are further needs for in vitro and in vivo models to assay the effectiveness and adjust parameters of such peritoneal dialysis methods.

SUMMARY

The present disclosure relates to compositions of peritoneal dialysis solutions and metabolizing enzymes, and their uses to treat disorders associated with pathologically elevated levels of metabolites, including, e.g., oxalate-associated disorders, such as oxalosis and hyperoxalemia. In some embodiments, peritoneal dialysis solutions supplemented with metabolizing enzymes can be administered to a mammal, e.g., via peritoneal dialysis, to effectively reduce oxalate levels in circulation of the mammal and/or to reduce damage caused by oxalate deposits. The compositions and methods of the invention can be easily and conveniently performed.

Peritoneal dialysis solutions supplemented with metabolizing enzymes or functional fragment thereof can enhance elimination of detrimental metabolites from plasma in patients receiving dialysis. For example, peritoneal dialysis solutions supplemented with oxalate-degrading enzymes can significantly improve the effectiveness of peritoneal dialysis in patients with oxalosis and kidney failure. The invention allows initially a fast degradation of the metabolite, e.g., oxalate, removed from blood into the peritoneal dialysis solution in the peritoneal cavity, which over time preserves or increases the gradient of metabolite between the patient's circulation and the peritoneal dialysis solution. Such a gradient further enhances elimination of the unwanted metabolite from circulation, resulting in significant reduction of the metabolite levels in plasma and consequent reduction of the metabolite levels in tissues, such as, e.g., in the eye, kidney, or liver. When the peritoneal dialysis solution is administered into the peritoneal cavity of a patient, the metabolizing enzyme in the solution degrades detrimental metabolites, such as, e.g., oxalate, in the peritoneal cavity. Accordingly, the peritoneal dialysis compositions and methods described herein can provide a significant improvement over existing dialysis methods. The compositions and methods described herein can remove the detrimental metabolites from circulation more quickly and effectively than existing peritoneal dialysis methods, thus allowing shorter and/or fewer sessions of peritoneal dialysis to be given to a patient. Furthermore, in a combined therapy with hemodialysis and peritoneal dialysis, the compositions and methods described herein can improve the efficacy of peritoneal dialysis and thus reduce the number and duration of hemodialysis sessions required, and consequently, the physical and financial suffering of a patient undergoing dialysis treatments can be reduced. Peritoneal dialysis using the compositions described herein will also show a significant advantage over other extracorporeal devices employing metabolizing enzymes to filer body fluid outside the body. In contrast to metabolizing enzymes that are confined in the extracorporeal device, the metabolizing enzymes can be administered using the compositions and methods of the invention to establish a gradient of the detrimental metabolite between different compartments of the body to facilitate and increase removal of the metabolite.

In a first aspect, the present disclosure provides a composition comprising a peritoneal dialysis solution and at least one metabolizing enzyme or a functional fragment thereof. In some embodiments, the metabolizing enzyme may be chosen from, for example, an oxalate-degrading enzyme (e.g., oxalate oxidase, oxalate decarboxylase, oxalyl-CoA decarboxylase, and formyl CoA transferase), a urate-degrading enzyme (e.g., urate oxidase (unease)), a urea-degrading enzyme (e.g., urease), a bilirubin-degrading enzyme (e.g., bilirubin oxidase), and a phenylalanine-degrading enzyme (e.g., phenylalanine hydroxylase, phenylalanine ammonia lyase). In some embodiments, the metabolizing enzyme is oxalate decarboxylase. In some embodiments, the metabolizing enzyme (e.g., oxalate-degrading enzyme) may be covalently modified, such as PEGylated. In some embodiments, the metabolizing enzyme may be soluble or crystallized. In some embodiments, the metabolizing enzyme may be crosslinked or uncrosslinked. In some embodiments, the metabolizing enzyme may comprise a sequence identical or substantially identical to an enzyme sequence found in a natural source, such as a plant, bacterium, or fungus. In some embodiments, the metabolizing enzyme may be recombinantly produced.

In some embodiments, the peritoneal dialysis solution may comprise at least one osmotic agent, at least one electrolyte, and at least one organic acid salt. In certain embodiments, the composition described herein can reduce oxalate levels in a mammal, such as oxalate levels in a biological fluid chosen from urine, blood, plasma, serum, and peritoneal fluid.

The present disclosure further provides a method of reducing metabolite, e.g., oxalate, concentration in a mammal. In some embodiments, the method may comprise administering the peritoneal dialysis solution described herein to the mammal. In some embodiments, the method may comprise preparing a peritoneal dialysis solution comprising at least one metabolizing enzyme, and administering the enzyme-supplemented peritoneal dialysis solution to the mammal. In some embodiments, the metabolizing enzyme may be chosen from, for example, an oxalate-degrading enzyme (e.g., oxalate oxidase, oxalate decarboxylase, oxalyl-CoA decarboxylase, and formyl CoA transferase), a urate-degrading enzyme (e.g., urate oxidase (uricase)), a urea-degrading enzyme (e.g., urease), a bilirubin-degrading enzyme (e.g., bilirubin oxidase), and a phenylalanine-degrading enzyme (e.g., phenylalanine hydroxylase, phenylalanine ammonia lyase), and functional fragments of any one of these enzymes. In some embodiments, the metabolite is chosen from oxalate, uric acid, urea, bilirubin, and phenylalanine. In some embodiments, the metabolite is oxalate. In some embodiments, the metabolizing enzyme is oxalate decarboxylase. Performing dialysis with a peritoneal dialysis solution comprising one or more metabolizing enzymes may increase the efficiency of oxalate removal and improve treatment of pathologic conditions associated with elevated levels of the metabolites relative to existing dialysis methods, including extracorporeal devices containing metabolizing enzymes. In some embodiments, the method may further comprise detecting metabolite, e.g., oxalate, concentration in a biological sample of the mammal, such as, e.g., urine, blood, plasma, scrum, or peritoneal fluid, from a patient suspected of suffering from a pathologically elevated level of metabolite. In some embodiments, peritoneal dialysis using the compositions and methods of the invention can result in reduction of metabolite, e.g., oxalate, concentration of at least 10%, such as at least 20%, at least 30%, or at least 40% or more. Such a reduction of concentration may be measured in a biological sample chosen from, for example, urine, blood, plasma, serum, and peritoneal fluid. In certain embodiments, the methods described herein can be combined with other methods of reducing metabolite concentration in a mammal, such as, e.g., hemodialysis. In another aspect, the present disclosure provides a method of treating, preventing, and/or slowing the progression of a disorder associated with elevated metabolite concentration in a mammal by administering the peritoneal dialysis solution of the invention to the mammal. In some embodiments, the method may comprise supplementing a peritoneal dialysis solution with at least one metabolizing enzyme, and administering the supplemented peritoneal dialysis solution to the mammal. In some embodiments, the metabolizing enzyme may be chosen from, for example, an oxalate-degrading enzyme (e.g., oxalate oxidase, oxalate decarboxylase, oxalyl-CoA decarboxylase, and formyl CoA transferase), a urate-degrading enzyme (e.g., urate oxidase (uricase)), a urea-degrading enzyme (e.g., urease), a bilirubin-degrading enzyme (e.g., bilirubin oxidase), and a phenylalanine-degrading enzyme (e.g., phenylalanine hydroxylase, phenylalanine ammonia lyase). In some embodiments, the metabolizing enzyme is oxalate decarboxylase. In some embodiments, the metabolite is chosen from oxalate, uric acid, urea, bilirubin, and phenylalanine. In some embodiments, the metabolite is oxalate. In some embodiments, the disorder may be chosen from oxalosis, hyperoxalemia, and hyperoxalemia secondary to a disease chosen from a kidney disorder, bone disorder, liver disorder, gastrointestinal disorder, and pancreatic disorder. For example, the disorder may be chosen from oxalosis, hyperoxalemia, primary hyperoxaluria, enteric hyperoxaluria, idiopathic hyperoxaluria, and hyperoxalemia secondary to a disease chosen from end stage renal disease, ethylene glycol poisoning, cystic fibrosis, inflammatory bowel disease, urolithiasis, nephrolithiasis, and chronic kidney disease. In some embodiments, the disorder is associated with elevated levels of uric acid, urea, bilirubin, or phenylalanine, such as, e.g., hyperuricemia, gout, uremia, hyperbilirubinemia, jaundice, hyperphenylalaninemia, and phenylketonuria (PKU). In certain embodiments, the methods described herein can be combined with other methods of treating elevated metabolite concentration, such as, e.g., hemodialysis.

Further provided is an animal model of hyperoxalemia. The animal model described herein may resemble conditions in patients with primary hyperoxaluria (PH) disease and/or end-stage renal disease (ESRD). In some embodiments, the model may comprise a non-human mammal, for example, a pig, administered with continuous infusion of oxalate. At the functional level, human and porcine species share many similarities in the gastrointestinal tract and genitourinary structures. Unlike rodents, human and swine have multipyramidal kidneys and comparable maximal urinary concentrations, glomerular filtration rates, and total renal blood flow characteristics. Mendel et al., *J Urol.* 171:1301-03 (2004); Kaplen et al., *J. Endourol.* 24:355-59 (2010). The mammal may be inserted with a first device for administering the continuous infusion of oxalate. In some embodiments, the first device may be e.g., a catheter or pleural trocair. The catheter may be inserted percutaneously with or without surgery. In some embodiments, the catheter may be a peripheral venous catheter, such as VENFLON™ or CATHLON™. In some embodiments, the mammal may be inserted with a second device, e.g., a catheter, for blood sampling. The animal model may be used to perform the methods described herein. As shown in the Examples, peritoneal dialysis (PD) performed in one embodiment of the animal models described herein may remove about 20%-30% of plasma oxalate during about 4-6 hours of treatment, which is usually one cycle of PD.

The details of one or more embodiments of the present disclosure are set forth in the accompanying drawings and the description below.

DESCRIPTION OF DRAWINGS

FIG. 1 shows the oxalate concentration in serum and peritoneal dialysis (PD) samples from pigs infused with different concentrations of oxalate (FIGS. 1*a* and 1*b*).

FIG. 2 shows the oxalate concentration in serum and peritoneal dialysis samples from a pig infused with oxalate and administered with PD (control) or PD+OXDC.

FIG. 3 shows a diagram of an in vitro dialysis model using PD solution GAMBROSOL TRIO™ 10±OXDC.

FIG. 4 shows the oxalate concentration in an in vitro dialysis model using GAMBROSOL TRIO™ 10±OXDC.

FIG. 5 shows a diagram of an in vitro dialysis model using serum and PD solution GAMBROSOL TRIO™ 10±OXDC.

FIG. 6 shows the oxalate concentration in an in vitro dialysis model using scrum and GAMBROSOL TRIO™ 10±OXDC.

FIG. 7 shows OXDC dosage-dependent reduction of in vitro serum oxalate levels.

DETAILED DESCRIPTION OF EXEMPLARY EMBODIMENTS

The present disclosure is based, in part, on compositions of peritoneal dialysis solutions and metabolizing enzymes. Also described herein are methods of administering the compositions to reduce metabolite concentrations and to treat conditions associated with elevated levels of one or more metabolites, for example, oxalate-related disorders. Further described herein are animal models of hyperoxalemia and peritoneal dialysis.

Definitions

In order that the present disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

The articles "a" and "an," as used herein, should be understood to mean "at least one," unless clearly indicated to the contrary.

The phrase "and/or" as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other that) B); in another embodiment, to at least one, optionally including more than one, B, with no A present (and optionally including elements other than A); in yet another embodiment, to at least one, optionally including more than one. A, and at least one, optionally including more than one, B (and optionally including other elements); etc.

As used herein, all transitional phrases such as "comprising," "including," "carrying," "having," "containing," "involving," "holding," and the like are to be understood to be open-ended, i.e., to mean including but not limited to. All compositions and solutions described herein should be considered to be modified by any of these terms.

Only the transitional phrases "consisting of" and "consisting essentially of" shall be closed or semi-closed transitional phrases, respectively, as set forth in the United States Patent Office Manual of Patent Examining Procedures. "Consisting of" excludes any unspecified element, step, or ingredient. "Consisting essentially of" only includes the specified elements, steps, and ingredients and those that do not materially affect the basic and novel characteristics of the compositions and solutions described herein. All compositions and solutions described herein should be considered to be modified by either or both of these terms.

A "biological sample" is biological material collected from cells, tissues, organs, or organisms, for example, to detect an analyte. Exemplary biological samples include a fluid, cell, or tissue sample. Biological fluids include, for example, serum, blood, plasma, saliva, urine, sweat, or peritoneal fluid. Cell or tissue samples include biopsy, tissue, cell suspension, or other specimens and samples, such as clinical samples.

A "crystal" is one form of the solid state of matter, comprising atoms arranged in a pattern that repeats periodically in three dimensions (see, e.g., Barret, Structure of Metals, 2nd ed., McGraw-Hill, New York (1952)). A crystal form of a polypeptide, for example, is distinct from a second form-the amorphous solid state. Crystals display characteristic features including shape, lattice structure, percent solvent, and optical properties, such as, e.g., refractive index. Crystals may be in crosslinked or uncrosslinked form.

A "functional fragment" of oxalate-degrading enzymes refers to a portion of an oxalate-degrading enzyme polypeptide that retains one or more biological activities of the enzyme, such as the ability to catalyze the decarboxylation or oxidation of oxalate. As used herein, a functional fragment may comprise terminal truncations from one or both termini, unless otherwise specified. For example, a functional fragment may have 1, 2, 4, 5, 6, 8, 10, 12, 15, or 20 or more residues omitted from the amino and/or carboxyl terminus of an oxalate-degrading enzyme polypeptide. In some embodiments, the truncations are not more than 20 amino acids from one or both termini. A functional fragment may optionally be linked to one or more heterogonous sequences.

The term "patient," "individual," or "subject" refers to any mammal, including but not limited to, any animal classified as such, including humans, non-human primates, primates, baboons, chimpanzees, monkeys, rodents (e.g., mice, rats), rabbits, cats, dogs, horses, cows, sheep, goats, pigs, etc.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80% 90% (w/w) pure, even more preferably, 90 to 95% pure; and, most preferably, at least 95%, 96%, 97%, 98%, 99%, 99.5%, 99.8% or 100% (w/w) pure.

A unit is defined as the amount of an enzyme that will degrade one microgram of a substrate per minute at 37° C. For example, a unit of oxalate decarboxylase is the amount of oxalate decarboxylase that will degrade one microgram of oxalate per minute at 37° C.

Conditions associated with elevated levels of a metabolite include, without limitation, oxalate-associated disorders, urate-associated disorders, urea-associated disorders, bilirubin-associated disorders, and phenylalanine-associated disorders. Such conditions and disorders may optionally be acute or chronic.

As used herein, "oxalate-associated disorder" refers to a disease or disorder associated with pathologic levels of oxalic acid or oxalate, including, but not limited to oxalosis, hyperoxalemia, hyperoxaluria, primary hyperoxaluria, enteric hyperoxaluria, idiopathic hyperoxaluria, end stage renal disease, ethylene glycol (oxalate) poisoning, idiopathic urinary stone disease, renal failure (including progressive, chronic, or end-stage renal failure), steatorrhoea, malabsorption, ileal disease, vulvodynia, cardiac conductance disorders, inflammatory bowel disease, cystic fibrosis, exocrine pancreatic insufficiency. Crohn's disease, ulcerative colitis, nephrocalcinosis, urolithiasis, and nephrolithiasis. Such conditions and disorders may optionally be acute or chronic, Oxlate-associated disorders associated with kidneys, bone, liver, gastrointestinal tract, and pancreas are known in the art. Further, it is well known that calcium oxalate can deposit in a wide variety of tissues including, but not limited to, the eyes, blood vessels, joints, bones, muscles, heart, and other major organs leading to a number of oxalate-associated disorders.

"Oxalic acid" exists predominantly in its salt form, oxalate (as salts of the corresponding conjugate base), at the pH of urine and intestinal fluid ($pK_{a1}$=1.23, $pK_{a2}$=4.19). Earnest, *Adv. Internal Medicine* 24:407 427 (1979). The terms "oxalic acid" and "oxalate" are used interchangeably throughout this disclosure. Oxalate salts comprising lithium, sodium, potassium, and iron (II) may be soluble, but calcium oxalate may be very poorly soluble in water (for example, dissolving only to about 0.58 mg/100 ml at 18° C. Earnest, *Adv. Internal Medicine* 24:407 427 (1979)). Oxalic acid from food may be also referred to as dietary oxalate. Oxalate that is produced by metabolic processes may be referred to as endogenous oxalate. Circulating oxalate may be the oxalate present in a circulating body fluid, such as blood.

The terms "therapeutically effective dose," or "therapeutically effective amount,"refer to that amount of a metabolizing enzyme or functional fragments thereof that results in reduced levels of metabolite in the blood and may include prevention, delay of onset of symptoms, or amelioration of symptoms of a condition, e.g., an oxalate-associated condition, including, but not limited to oxalosis, hyperoxalemia, and hyperoxaluria, such as primary hyperoxaluria or enteric hyperoxaluria. A therapeutically effective amount may, for example, be sufficient to treat, prevent, reduce the severity, delay the onset, and/or reduce the risk of occurrence of one or more symptoms of a disorder associated with elevated oxalate concentrations.

Dialysis Solution

The terms "dialysis solution," "dialysis fluid," and "dialysate" are used herein interchangeably. A dialysis solution refers to an aqueous fluid having the proper solutes in the proper concentrations for peritoneal dialysis. Peritoneal dialysis may include, for example, continuous ambulatory peritoneal dialysis (CAPD), intermittent peritoneal dialysis (IPD), continuous cyclic peritoneal dialysis (CCPD), automated peritoneal dialysis (APD), continuous flow peritoneal dialysis (CFPD), regenerative peritoneal dialysis (RPD), and continuous flow regenerative peritoneal dialysis (CFRPD).

In some embodiments, the dialysis solution used for peritoneal dialysis may comprise an aqueous solution comprising at least one osmotic agent, at least one electrolyte, and at least one organic acid salt. In some embodiments, an osmotic agent may be chosen from, for example, glucose, icodextrin, and amino acids. In some embodiments, an electrolyte may be chosen from, for example, sodium, potassium, calcium, and magnesium. In some embodiments, an organic acid salt may be chosen from, for example, lactate, bicarbonate, and pyruvate salts. The pH of the peritoneal dialysis solution described herein may range from 5 to 8. In some embodiments, the pH may vary range from 5.2 to 7.4, such as from 6.0 to 7.4, and from 7.0 to 7.4. In some embodiments, the peritoneal dialysis solutions described herein may also comprise biologically active agents that reduce oxalate levels or that increase the activity or availability of metabolizing enzymes. The components of the peritoneal dialysis solutions described herein may be selected to control the levels of electrolytes or the acid-base equilibrium, to remove waste materials, to efficiently carry out ultrafiltration, and/or to manipulate the activity of the metabolizing enzymes described herein.

The peritoneal dialysis solutions described herein may be chosen from single-chamber and multi-chamber dialysis solutions. Multi-chamber dialysis solutions are known in the art, such as those described in, e.g., WO 99/27885. Different solutes may thus be kept in separate compartments with a view to, inter alia, regulating the concentration of active ingredients in the finally prepared solution. Peritoneal dialysis solutions may be purchased from commercial purveyors, for example, Baxter (e.g., PHYSIONEAL™, DIANEAL™, EXTRANEAL™, or NUTRINEAL™), Gambro (e.g., GAMBROSOL TRIO™), and Fresenius (e.g., BALANCE™, or BICAVERA™). Various kinds of peritoneal dialysis solutions and preparation methods thereof are known in the art. See, e.g., de Vin et al., *Peril. Dial. Int.* 29:5-15 (2009); Schmitt et al., *Pediatr. Nephrol.* 26:1137-47 (2011); Garcia-López et al., *Nat. Rev. Nephrol.* 8:224-33 (2012).

In some embodiments, the peritoneal dialysis solution may also include an agent to accelerate peritoneal dialysis, such as, e.g., a surface-active agent or wetting agent (see, e.g., Penzotti et al., *J Pharm Sci* 57(7): 1192-95 (1968)). In some embodiments, the wetting agent may be anionic, cationic, or nonionic. In certain embodiments, the wetting agent is dactyl sodium sulfosuccinate. In some other embodiments, the agent to accelerate peritoneal dialysis is catecholamine, such as, e.g., one chosen from norepinephrine and dopamine (see, e.g., Hirszel et al., *J Lab Clin Med.* 94(5):747-54 (1979)). In certain embodiments, the agent is dopamine.

As used herein, a metabolizing enzyme refers to an enzyme that is capable of reacting with a product of human or animal metabolism, including, for example, enzymes capable of degrading uric acid, urea, or oxalate.

Urate Oxidase (Uricase)

The terms "urate oxidase" and "uricase" are used herein interchangeably. Urate oxidase (uricases; E.C. 1.7.3.3) refers to a urate oxidase enzyme. Urate oxidases include a group of well-defined enzymes capable of catalyzing the oxidation of uric acid to a more soluble product, allantoin, a purine metabolite that is more readily excreted:

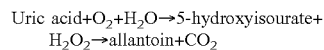

Uric acid+$O_2$+$H_2O$→5-hydroxyisourate+ $H_2O_2$→allantoin+$CO_2$

Elevated levels of uric acid in the blood can cause hyperuricemia and gout. Isoforms of urate oxidase, and glycoforms of those isoforms, are included within this definition. Urate oxidases from plants, bacteria and fungi are encompassed by the term, including the true urate oxidases from bacteria and fungi, such as *Aspergillus flavus*. In certain circumstances, urate oxidase may be a soluble or insoluble tetrameric protein. The cDNA coding for this protein has been cloned and expressed in *Escherichia coli* (Legoux et al., *J. Biol. Chem.*, 267:8565-8570 (1992)), in *Aspergillus flavus* (Chevalet et al., *Curr. Genet* 21:447-453 (1992)), and in *Saccharomyces cerevisiae* (Leplatois et al., *Gene* 122, 139-145 (1992)). Recombinant urate oxidases include urate oxidases produced by genetically modified microorganisms and can, for example, be obtained from the above mentioned genetically modified strains of *Escherichia coli* and *Saccharomyces cerevisiae*. Rasburicase refers to a recombinant urate oxidase enzyme produced from genetically modified strain of *Saccharomyces cerevisiae* cloned with cDNA from a strain of *Aspergillus flavus* (Oldfield et al., *Drugs* 66 (4):529-545 (2006), Leplatois et al., *Gene* 122:139-145(1992)). Rasburicase includes a tetrameric protein with identical subunits of a molecular mass of about 34 kDa each, similar to the native *Aspergillus flavus* urate oxidase (Bayol et. al., *Biotechnol. Appl. Biochem.* 36:21-31 (2002

Urease

Urease (EC 3.5.1.5) refers to a urease enzyme. Ureases include a group of well-defined enzymes capable of catalyzing the hydrolysis of urea into carbon dioxide and ammonia:

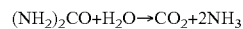

$(NH_2)_2CO+H_2O \rightarrow CO_2+2NH_3$

High level of urea results in uremia and is often accompanying kidney failure. Isoforms of urease, and glyoforms of those isoforms, are included within this definition. Ureases from plants, bacteria and fungi are encompassed by the term, including the true Ureases from bacteria and fungi, such as *Ureaplasma urealyticum, Actinomyces naeslundii, Yersinia pestis, Filobasidiella neoformans, Coccldioldes immitis, Bordetella bronchiseptica, Streptococcus salivarius, Mycobacterium tuberculosis, Actinobacillus pleuropneumoniae, Thermophilic Bacillus, Ureaplasma urealyticum, Ureaplasma urealyticum, Yersinia pseudotuberculosis, Canavalia ansiformis, Bacillus pasteurli, Heliobacter hellmannil, Yersinia enterocolitica, Pintirabilis, Klebsiella aerogenes, Klebsiella pneumonia. Helicobacter pylori*, and *Escherichia coli*.

As used herein, oxalate-degrading enzyme refers to enzymes that are capable of catalyzing the degradation of oxalate. In some embodiments, oxalate-degrading enzymes may include, for example, oxalate oxidase, oxalate decarboxylase, oxalyl-CoA decarboxylase, and formyl CoA transferase. E.g., Svedruzie et al., *Arch Biochem. Biophys.* 433: 176-92 (2005).

Oxalate Oxidase

As used herein, oxalate oxidase (OXO) (EC 1.2.3.4) refers to an oxalate: oxygen oxidoreductase enzyme. Oxalate oxidases include a group of well-defined enzymes capable of catalyzing the molecular oxygen ($O_2$)-dependent oxidation of oxalate to carbon dioxide and hydrogen peroxide according to the following reaction.

$$HO_2C-CO_2H + O_2 \rightarrow 2CO_2 + H_2O_2$$

Isoforms of oxalate oxidase, and glycoforms of those isoforms, are included within this definition. OXO from plants, bacteria and fungi are encompassed by the term, including the true cereal OXOs, such as wheat, barley, maize, oat, rice, and rye. These enzymes may be identified as germin-type OXOs (G-OXOs), because wheat oxalate oxidase is also known as germin. The germin-like proteins (GLPs) include a large class of proteins sharing certain structural features. Other sources of OXO include moss, beet, spinach, sorghum, and banana, OXOs, such as G-OXOs, may be active as, for example, hexameric glycoproteins. Optionally, OXOs may additionally be capable of superoxide dismutase activity, such as barley OXO. In certain circumstances, OXO may be a soluble hexameric protein, including a trimer of OXO glycoprotein dimers.

Oxalate Decarboxylase

As used herein, oxalate decarboxylase (OXDC) (EC 4.1.1.2) refers to an oxalate carboxylase enzyme. Oxalate decarboxylases include a group of enzymes known in the art to be capable of catalyzing the molecular oxygen ($O_2$) independent oxidation of oxalate to carbon dioxide and formate according to the following reaction:

$$HO_2C-CO_2H \rightarrow 1CO_2 + HCOOH$$

Isoforms of oxalate decarboxylase, and glyoforms of those isoforms, are included within this definition. OXDC from plants, bacteria and fungi are encompassed by the term, including the true oxalate decarboxylases from bacteria and fungi, such as *Bacillus subtilis, Collybia velutipes* or *Flammulina velutipes, Aspergillus niger, Pseudomonas* sp., *Synechocystis* sp., *Streptococcus mutans, Trametes hirsute, Sclerotinia sclerotiorum, T. versicolor, Postia placenta, Myrothecium verrucaria, Agaricus bisporus, Methylobacterium extorquens, Pseudomonas oxalaticus, Ralstonio eutropha, Cupriavidus oxalaticus, Wautersia* sp., *Oxalicibacterium flavum, Ammoniiphilus oxalaticus. Vibro oxalaticus, A. oxalativorans, Variovorax paradoxus, Xanthobacter autotrophics, Aspergillus* sp., *Penicillium* sp., and *Mucor* species. Optionally, the OXDC will be additionally dependent on coenzyme A, such as OXDC from organisms in the intestinal tract. In certain circumstances, OXDC may be a soluble or insoluble hexameric protein.

Oxalyl-CoA Decarboxylase and Formyl CoA Transferase

As used herein, oxalyl-CoA decarboxylase (OXC) (EC 4.1.1.8) refers to an oxalyl-CoA decarboxylase enzyme. Formyl-CoA transferase (FRT) (EC 2.8.3.16) refers to a formyl-CoA transferase enzyme. Oxalyl-CoA decarboxylases include a group of enzymes known in the art to be capable of catalyzing conversion of oxalyl-CoA into formyl-CoA and carbon dioxide:

$$\text{oxalyl-CoA} \rightleftharpoons \text{formyl-CoA} + CO_2$$

Formyl-CoA transferases include a group of enzymes known in the art to be capable of exchanging formate and oxalate on CoA:

$$\text{formyl-CoA} + \text{oxalate} \rightleftharpoons \text{formate} + \text{oxalyl-CoA}$$

Thus, oxalate can be converted into formate and carbon dioxide through the combined action of oxalyl-CoA decarboxylase and formyl-CoA transferase. Isoforms of OXC and FRC, and glycoforms of those isoforms, are included within this definition. OXC and FRC from plants, bacteria and fungi are encompassed by the term, including the enzymes from bacteria and fungi, such as *Pseudomonas oxalaticus* and *Oxalobacter formigenes*. In certain circumstances, OXC may be a soluble or insoluble tetrameric protein.

Bilirubin Oxidase

Bilirubin oxidase (BO) (EC 1.3.3.5) refers to an enzyme which catalyzes a reaction for oxidizing bilirubin into biliverdin and is one kind of enzyme belonging to a multicopper oxidase (a general term of an enzymes having plural copper ions in the active center). The enzyme catalyzes the chemical reaction:

$$2 \text{ bilirubin} + O_2 \rightleftharpoons 2 \text{ biliverdin} + 2H_2O$$

The enzyme also includes bilirubin oxidase M–1, which participates in porphyrin and chlorophyll metabolism. Tanaka et al. *Agric. Biol. Chem.* 49: 843-844 (1985). Higher than normal level of bilirubin in the blood results in hyperbilirubinemia and is also associated with jaundice. Isoforms of BO, and glycoforms of those isoforms, are included within this definition. BO from plants, bacteria and fungi are encompassed by the term, such as, e.g., the enzymes from *Myrothecium verrucaria*. Mizutani et al., *Acta Cryst.* F66 (7): 765-770 (2010); Cracknell et al., *Dalton Trans.* 40 (25): 765-770 (2011).

Phenylalanine Hydroxylase

Phenylalanine hydroxylase (PAH, PheOH, or PheH) (EC 1.14.16.1) refers to an enzyme that catalyzes the hydroxylation of the aromatic side-chain of phenylalanine to generate tyrosine, which is the rate-limiting step in the catabolism of Phe. The brain is highly sensitive to levels of Phe, and deficiencies in the PAH enzyme may result in excess levels of Phe or hyperphenylalanemia. Deficiencies in PAH enzyme activity may range from classical phenylketonuria (PKU) and its potential for severe central nervous system dysfunction (mental retardation), to moderate elevations in plasma Phe with no known clinical consequences. A deficiency in PAH enzyme activity is the most common cause of hyperphenylalanemia. The human PAH gene spans 90 kb, is comprised of 13 exons, and has been localized to chromosome 12q24.1. Lidsky et al., *Proc Natl Acad Sci USA*, 82:6221-6225 (1985); Ditella et al., *Biochemistry*, 25:743-749 (1986). Structure and function of human PAH have been studied. Hofton et al., *Biochem J,* 311:353-366 (1995); Waters et al., *Hum Mutat.* 11:4-17 (1998). Isoforms of PAH, and glycoforms of those isoforms, are included within this definition. PAH from other sources are encompassed by the term.

Phenylalanine Ammonia Lyase

Phenylalanine ammonia lyase (PAL; EC 4.3.1.5) refers to an enzyme that catalyzes a reaction converting L-phenylalanine to ammonia and trans-cinnamic acid. The enzyme has a potential role in the treatment and diagnosis of phenylketonuria (PKU). Ambrus et al., *Science,* 201:837-839 (1978). PAL may be derivable from a microorganism, in particular a fungus such as *Rhodotorula* sp., *Rhodosoridium* sp., *Sporobolus* sp., *Geotrichum* sp., *Moniliella* sp., *Pellicularia* sp., *Gonatobotryum* sp., *Syncerhalastrum* sp., *Endomyces* sp., *Aspergillus* sp., *Saccharomvcopsis* sp., *Eurotium* sp., *Glomerella* sp., *Cladosporium* sp. or *Trichosporon* sp., or from a plant such as *Pisum sativum*, potato, sweet potato or soy bean.

Isolated Metabolizing Enzymes

Metabolizing enzymes used to prepare the peritoneal dialysis solutions of the invention, may be isolated, for example, from a natural source, or may be derived from a natural source. As used herein, the term "derived from" means having an amino acid or nucleic acid sequence that naturally occurs in the source. For example, oxalate oxidase derived from barley may comprise a primary sequence of a barley oxalate oxidase protein, or may be encoded by a nucleic acid comprising a sequence found in barley that encodes an oxalate oxidase or a degenerate thereof. Oxalate decarboxylase derived from *Bacillus subtilis* may comprise a primary sequence of a *Bacillus subtilis* oxalate decarboxylase protein, or may be encoded by a nucleic acid comprising a sequence found in *Bacillus subtilis* that encodes an oxalate decarboxylase or a degenerate thereof. Oxalyl-CoA decarboxylase or formyl CoA transferase derived from *Oxalobacter formigenes* may comprise a primary sequence of an *Oxalobacter formigenes* oxalyl-CoA decarboxylase or formyl CoA transferase protein, or may be encoded by a nucleic acid comprising a sequence found in *Oxalobacter formigenes* that encodes an oxalyl-CoA decarboxylase or formyl CoA transferase, or a degenerate thereof. A protein or nucleic acid derived from a source encompasses molecules that are isolated from the source, recombinantly produced, and/or chemically synthesized or modified. The composition provided herein may comprise polypeptides comprising amino acid sequences of a metabolizing enzyme or from a functional fragment of the enzyme that retains oxalate degrading activity. In some embodiments, the enzyme may retain at least one functional characteristic of a naturally occurring enzyme, e.g., the ability to catalyze degradation of oxalate, the ability to multimerize, ion (e.g., manganese) requirement, and/or other catalytic capabilities (e.g., superoxide dismutase activity).

Oxalate oxidases have been previously isolated and are thus available from many sources, including barley seedlings, roots, and leaves, beet stems, beet leaves, wheat germ, sorghum leaves, and banana peel. OXO may also be purchased from commercial purveyors, such as, e.g., Sigma. Methods to isolate OXO front a natural source are previously described, for example, in the following references: Liu et al., *Zhi Wu Sheng Li Yu Fen Zi Sheng Wu Xue Xue Bao* 30:393-8 (2004) (Engl. Abst. at PMID 15627687); Rodriguiez-Lopez et al., *FEBS Lett.* 9:44-48 (2001); Pundir et al., *Chin. J. Biotechnol.* 15: 129-138 (1999); and Aguilar et al., *Arch. Biochem. Biophys.* 366:275-82 (1999). These isolated oxalate oxidases may be used to form the compositions described herein.

Oxalate decarboxylases have been previously isolated and are thus available from many sources, including *Bacillus subtilis, Collybia velutipes* or *Flammulina velutipes, Aspergillus niger, Pseudomonas* sp., *Synechocystis* sp., *Streptococcus mutans, Trametes hirsute, Sclerotinia sclerotiorum, T. versicolor, Postia placenta, Myrothecium verrucaria, Agaricus bisporus, Methylobacterium extorquens, Pseudomonas oxalaticus, Ralstonia eutropha, Cupriavidus oxalaticus, Wautersia* sp., *Oxalicibacterium flavum, Ammoniiphilus oxalaticus, Vibrio oxalaticus, A. oxalativorans, Variovorax paradoxus, Xanthobacter autotrophicus, Aspergillus* sp., *Penicillium* sp., and *Mucor* species. OXDC may also be purchased from commercial purveyors, such as, e.g., Sigma. Methods to isolate OXDC from a natural source are previously described, for example, in the following references: Tanner et al., *The Journal of Biological Chemistry* 47: 43627-43634. (2001); Dashek et al., *Methods in plant biochemistry and molecular biology*. Boca Raton, Fla.: CRC Press. 5:49-71. (1997); Magro et al., *FEMS Microbiology Letters*. 49: 49-52. (1988); Anand et al., *Biochemistry*. 41: 7659-7669. (2002); and Tanner and Bomemann, *Journal of Bacteriology*. 182:5271-5273 (2000). These isolated oxalate decarboxylases may be used to form the compositions described herein.

Oxalyl-CoA decarboxylases and formyl CoA transferases have been previously isolated and are thus available from many sources, including oxalate degrading bacteria, *Pseudomonas oxalaticus* present in the soil (Qyayle et al., *Biochem. J.* 78:611-615 (1961)) and *Oxalobacter formigenes* residing in the gastro-intestinal tract of vertebrates, including humans (Allison et al., *Arch. Microbiol.* 141:47 (1985)). OXC and FRT may also be purchased from commercial purveyors, such as, e.g., Sigma. Both enzymes as well as the membrane transporter for the oxalate-formate exchange have also been purified and well characterized (Baetz and Allison. *J. Bact.* 171:2605-2608 (1989); Baetz and Allison, *J. Bact.* 172:3537-3540 (1990): Ruan et al., *J. Biol. Chem.* 267:10537-19543 (1992)). These isolated oxalyl-CoA decarboxylases and/or formyl CoA transferases may be used to form the compositions described herein.

Recombinant Metabolizing Enzymes

Alternatively, recombinant metabolizing enzymes may be used to form the compositions provided herein. In some embodiments, recombinant metabolizing enzyme may encompass or be encoded by sequences from a naturally occurring enzyme sequence. Furthermore, metabolizing enzymes comprising an amino acid sequence that is homologous or substantially identical to a naturally occurring sequence are herein described. Also, metabolizing enzymes encoded by a nucleic acid that is homologous or substantially identical to a naturally occurring enzyme-encoding nucleic acid are provided and may be used as described herein.

Polypeptides referred to herein as "recombinant" include polypeptides which have been produced by recombinant DNA methodology, including those that are generated by procedures which rely upon a method of artificial recombination, such as the polymerase chain reaction (PCR) and/or cloning into a vector using restriction enzymes. "Recombinant"polypeptides also include polypeptides having altered expression, such as a naturally occurring polypeptide with recombinantly modified expression in a cell, such as a host cell.

In some embodiments, OXO may be recombinantly produced from a nucleic acid that is homologous to a barley OXO nucleic acid sequence, and sometimes it may be modified, e.g., to increase or optimize recombinant production in a heterogonous host. An example of such a modified sequence includes the nucleic acid sequence of the open reading frame of barley OXO. The OXO sequence can be modified to reduce its GC content, is linked to an α Mating Factor secretion signal sequence, and is flanked by engineered restriction endonuclease cleavage sites. In some embodiments, OXO may be recombinantly produced from an unmodified barley nucleic acid sequence that is available at GenBank Accession No: L15737.

In some embodiments, OXDC may be recombinantly produced from a nucleic acid that is homologous to a *Bacillus subtilis* or *Collybia velutipes* OXDC nucleic acid sequence, and sometimes it may be modified, e.g., to increase or optimize recombinant production in a heterologous host. An example of such a modified sequence includes the nucleic acid sequence of the open reading frame of *Collybia velutipes* OXDC, for expression in *Candida boidinli*. The OXDC sequence can be modified to reduce its GC content, is linked to an a Mating Factor secretion signal sequence, and is flanked by engineered restriction endonuclease cleavage sites. In some embodiments, OXDC may be recombinantly produced from the unmodified *Bacillus subtilis* OXDC nucleic acid sequence which is available at GenBank Accession No:Z99120.

In some embodiments, OXC or FRT may be recombinantly produced from a nucleic acid that is homologous to a *Pseudomonas oxalaticus* or *Oxalobacter formigenes* OXC or FRT nucleic acid sequence, and sometimes it may be modified, e.g., to increase or optimize recombinant production in a heterologous host. In some embodiments, OXC may be recombinantly produced from the *Oxalobacter formigenes* OXC nucleic acid sequence. In some embodiments, FRT may be recombinantly produced from the *Oxalobacter formigenes* FRT nucleic acid sequence.

Also, the genes for all three proteins have been cloned, sequenced and expressed as biologically active recombinant proteins (Abe et al., *J. Biol. Chem.* 271:6789-6793 (1996); Lung et al., *J. Bact.* 179:3378-3381 (1994); Sidhu et al., *J. Bact.* 179:3378-3381 (1997)).

In some embodiments, metabolizing enzymes useful for forming the compositions described herein may be expressed in a host cell, such as a host cell comprising a nucleic acid construct that includes a coding sequence for a metabolizing enzyme polypeptide or a functional fragment thereof. A suitable host cell for expression of the enzyme may include, for example, yeast, bacteria, fungus, insect, plant, or mammalian cell, or transgenic plants, transgenic animals, or a cell-free system. In some embodiments, a host cell may be capable of glycosylating the enzyme polypeptide if necessary, capable of disulfide linkages, capable of secreting the enzyme, and/or capable of supporting multimerization of enzyme polypeptides. Exemplary host cells include, but are not limited to *E. coli* (including *E. coli* Origami B and *E. coli* BL21), *Hansenula polymorpha, Pichia pastoris, Saccharomyces cerevisiae, Schizosaccharomyces pombe, Bacillus subtilis,* Aspergillus, S19 cells, Chinese hamster ovary (CHO), 293 cells (human embryonic kidney), and other human cells. Also transgenic plants, transgenic animals including pig, cow, goat, horse, chicken, and rabbit may be suitable hosts for production of the enzyme described herein.

For recombinant production of a metabolizing enzyme, a host or host cell may comprise a construct in the form of a plasmid, vector, phagemid, or transcription or expression cassette that comprises at least one nucleic acid encoding a metabolizing enzyme or a functional fragment thereof. A variety of constructs are available, including constructs which are maintained in single copy or multiple copies, or which become integrated into the host cell chromosome. Many recombinant expression systems, components, and reagents for recombinant expression are commercially available, for example from Invitrogen Corporation (Carlsbad, Calif.); U.S. Biological (Swampscott, Mass.); BD Biosciences Phanningen (San Diego, Calif.); Novagen (Madison, Wis.); Stratagene (La Jolla, Calif.); and Deutsche Sammlung von Mikroorganismen und Zellkulturen GmbH (DSMZ). (Braunschwcig, Germany).

In some embodiments, recombinant expression of metabolizing enzymes may be optionally controlled by a heterogonous promoter, including a constitutive and/or inducible promoter. Promoters such as, e.g., T7, the alcohol oxidase (AOX) promoter, the dihydroxy-acetone synthase (DAS) promoters, the Gal 1,10 promoter, the phosphoglycerate kinase promoter, the glyceraldehyde-3-phosphate dehydrogenase promoter, alcohol dehydrogenase promoter, copper metallothionein (CUP1) promoter, acid phosphatase promoter, CMV and promoters polyhedrin may also be appropriate. The particular promoter may be selected based on the host or host cell. In addition, promoters that are inducible by methanol, copper sulfate, galactose, by low phosphate, by alcohol, e.g., ethanol, for example, may also be used and are well known in the art.

In some embodiments, a nucleic acid that encodes metabolizing enzymes may optionally comprise heterologous sequences. For example, a secretion sequence may be included at the N-terminus of an enzyme polypeptide in some embodiments. Signal sequences such as those from a Mating Factor, BGL2, yeast acid phosphatase (PHO), xylanase, alpha amylase, from other yeast secreted proteins, and secretion signal peptides derived from other species that are capable of directing secretion from the host cell may be useful. Similarly other heterogonous sequences such as linkers (e.g., comprising a cleavage or restriction endonuclease site) and one or more expression control elements, an enhancer, a terminator, a leader sequence, and one or more translation signals are within the scope of this description. These sequences may optionally be included in a construct and/or linked to the nucleic acid that encodes the enzymes. Unless otherwise specified, "linked" sequences can be directly or indirectly associated with one another.

Similarly, an epitope or affinity tag such as Histidine, HA (hemagglutinin peptide), maltose binding protein, AviTag®, FLAG, or glutathione-S-transferase may be optionally linked to the enzyme polypeptide. A tag may be optionally cleavable from the enzyme after it is produced or purified. A skilled artisan can readily select appropriate heterogonous sequences, for example, match host cell, construct, promoter, and/or secretion signal sequence.

Enzyme homologs or variants may differ from an enzyme reference sequence by one or more residues. Structurally similar amino acids can be substituted for some of the specified amino acids, for example. Structurally similar amino acids include, for example, (I, L and V); (F and Y); (K and R); (Q and N); (D and E); and (G and A). Deletion, addition, or substitution of amino acids is also encompassed by the enzyme homologs described herein. Such homologs and variants include, for example, (i) polymorphic variants and natural or artificial mutants, (ii) modified polypeptides in which one or more residues is modified, and (iii) mutants comprising one or more modified residues.

An enzyme polypeptide or nucleic acid is "homologous" (or is a "homolog") if it is at least 40%, 50%, 60%, 70%, 75%, 80%, 85%, 90%, 95%, 97%, 98%, 99%, or 100% identical to a reference sequence. If the homolog is not identical to the reference sequence, it is a "variant." A homolog is "substantially identical" to a reference enzyme sequence if the nucleotide or amino acid sequence of the homolog differs from the reference sequence (e.g., by truncation, deletion, substitution, or addition) by no more than 1, 2, 3, 4, 5, 8, 10, 20, or 50 residues, and retains (or encodes a polypeptide that retains) the ability to catalyze the degradation of the enzymatic substrate. Fragments of a metabolizing enzyme may be homologs, including variants and/or substantially identical sequences. By way of example, homologs may be derived from various sources of the enzyme, or they may be derived from or related to a reference sequence by truncation, deletion, substitution, or addition mutation. Percent identity between two nucleotide or amino acid sequences may be determined by standard alignment algorithms such as, for example, Basic Local Alignment Tool (BLAST) described in Altschul et al., *J. Mol Biol.,* 215:403 410 (1900), the algorithm of Needleman et al., *J. Mol. Biol.*, 48:444 453 (1970), or the algorithm of Meyers et al., *Comput. Appl. Biosci.*4:11 17 (1988). Such algorithms are incorporated into the BLASTN, BLASTP, and "BLAST 2 Sequences" programs (reviewed in McGinnis and Madden, *Nucleic Acids Res.* 32:W20-W25, 2004). When utilizing such programs, the default parameters can be used. For example, for nucleotide sequences the following settings can be used for "BLAST 2 Sequences"; program BLASTN, reward for match 2, penalty for mismatch 2, open gap and extension gap penalties 5 and 2 respectively, gap x_dropoff 50, expect 10, word size 11, filter ON. For amino acid sequences the following settings can be used for "BLAST 2 Sequences"; program BLASTP, matrix BLOSUM62, open gap and extension gap penalties 11 and 1 respectively, gap x_dropoff50, expect 10, word size 3, filter ON. The amino acid and nucleic acid sequences for metabolizing enzymes that are appropriate to form the compositions described herein may include homologous, variant, or substantially identical sequences. In some embodiments, an enzyme homolog may retain at least 40%, 50%, 60%, 70%, 75%, 80%, 85%, 90%, 95%, 97%, 98%, 99%, or 100% activity relative to a reference sequence.

Purification of Metabolizing Enzymes

Proteins or polypeptides of the enzymes described herein may be purified from the source, such as a natural or recombinant source. A polypeptide that is referred to herein as "isolated" is a polypeptide that is substantially free of its natural environment, such as proteins, lipids, and/or nucleic acids of their source of origin (e.g., cells, tissue (e.g., plant tissue), or fluid or medium (in the case of a secreted polypeptide)). Isolated polypeptides include those obtained by methods described herein or other suitable methods, and include polypeptides that are substantially pure or essentially pure, and polypeptides produced by chemical synthesis, by recombinant production, or by combinations of biological and chemical methods. Optionally, an isolated protein may have undergone further processing after its production, such as by purification steps.

In some embodiments, purification may comprise buffer exchange and chromatographic steps. Optionally, a concentration step may be used, e.g., by dialysis, chromatofocusing chromatography, and/or associated with buffer exchange. In certain embodiments, cation or anion exchange chromatography may be used for purification, including Q-sepharose, DEAE sepharose, DE52, sulfopropyl Sepharose chromatography or a CM52 or similar cation exchange column. Buffer exchange optionally precedes chromatographic separation, and may be performed by tangential flow filtration such as diafiltration. In certain preparations, the metabolizing enzymes may be at least 70%, 80%, 85%, 90%, 95%, 96%, 97%, 98%, 99%, 99.5%, 99.7%, or 99.9% pure.

In some embodiments, purification in gram-scale runs may be appropriate to prepare metabolizing enzymes, and procedures may be optimized for efficient, inexpensive, manufacturing-scale enzyme purification. For example, purification of at least 0.5, 1, 2, 5, 10, 20, 50, 100, 500, or 1000 grams or more of metabolizing enzymes in a purification procedure is provided. In one exemplary procedure, tangential flow filtration of starting samples of at least 10 L, 50 L, 100 L, 500 L, 1000 L or more is provided, allowing buffer exchange and precipitation of contaminant proteins. A single Q-sepharose column may be optionally used for purification of the enzymes described herein.

In some embodiments, the metabolizing enzyme described herein, e.g., the oxalate-degrading enzyme, may be soluble or crystallized. Crystals of the enzymes can be prepared and/or dried using methods known in the art (see e.g., WO 2006/135926 and WO 2008/105911). In some embodiments, the enzymes may not be crystallized. In some embodiments, the enzymes may be covalently modified, such as PEGylated. For PEGylation methods, see e.g., U.S. Pat. No. 6,783,965. In some embodiments, the enzymes may be cross-linked. In some other embodiments, the enzymes may not be cross-linked. In some embodiments, the enzyme may be a cross-linked crystal (see. e.g., U.S. Pat. No. 6,004,768).

Methods of Treating Metabolite-Associated Disorders

The methods of the invention may comprise administering the peritoneal dialysis solution described herein to a mammalian subject in a therapeutically effective amount to treat, prevent, or reduce the risk of occurrence of a condition associated with high levels of metabolites, e.g., oxalate. In some embodiments, the method may comprise preparing a supplemented peritoneal dialysis solution comprising at least one metabolizing enzyme and administering the supplemented peritoneal dialysis solution to the mammalian subject. The elevated levels of metabolite, e.g., oxalate, may be detected, e.g., in a biological sample from the subject, such as a body fluid, including, for example, urine, blood, serum, plasma, or peritoneal fluid. In certain embodiments, urinary or serum oxalate levels may be detected. In some embodiments, the metabolite is chosen from oxalate, uric acid, urea, bilirubin, and phenylalanine. In some embodiments, the metabolite is oxalate.

In some embodiments, methods are provided for treating in individuals with, for example, oxalosis, hyperoxalemia, primary hyperoxaluria, enteric hyperoxaluria, (including, e.g., hyperoxaluria caused by surgical intervention), idiopathic hyperoxaluria. In other instances, oxalosis and/or hyperoxalemia secondary to elevated oxalate-related disorders of the kidneys (including, e.g., end-stage renal disease), bone, liver gastrointestinal tract and pancreas may be amenable to treatment with the methods disclosed herein. Further disorders or diseases treated by the methods provided herein may include, but are not limited to, oxalosis and/or hyperoxalemia secondary to the following conditions: ethylene glycol (oxalate) poisoning, idiopathic urinary stone disease, renal failure (including progressive, chronic, or end-stage renal failure), steatorrhoea, malabsorption, ileal disease, vulvodynia, inflammatory bowel disease, cystic fibrosis, exocrine pancreatic insufficiency, Crohn's disease, ulcerative colids, nephrocalcinosis, osteoporosis, urolithiasis, and nephrolithiasis. Such conditions and disorders may optionally be acute or chronic. In some embodiments, the disorder is associated with elevated level of uric acid, urea, bilirubin, or phenylalanine. In some embodiments, the disorder is chosen from hyperuricemia, gout, uremia, hyperbilirubinemia, jaundice, hyperphenylalaninemia, and phenylketonuria (PKU). In certain embodiments, the methods described herein can be combined with other methods of reducing metabolite concentration in a mammal, such as, e.g., hemodialysis.

In some embodiments, the methods of the invention may reduce, metabolite, e.g., oxalate, levels in a subject by at least 10%, 15%, 20%, 25%, 30%, 35%. 40%, 45%, 50%, 55%. 60%, 65%, 70%, 75%, 80%, 85%, 90%, 95%, or more as compared to levels in an untreated or control subject. In some embodiments, reduction is measured by comparing the metabolite level in a subject before and after administration of the composition. In some embodiments, the present disclosure provides a method of treating or ameliorating an metabolite-associated condition or disorder, to allow one or more symptoms of the condition or disorder to improve by at least 10%, 15%. 20%, 25%, 30%, 35%, 40%, 45%, 50%.

55%, 60%, 65%. 70%, 75%, 80%, 85%, 90%, 95% or more. In certain embodiments, the methods may reduce levels of endogenous oxalate and/or adsorption of dietary oxalate.

In some embodiments, methods for treating individuals having a genotype associated with high oxalate levels are provided, such as individuals homozygous or heterozygous for a mutation that reduces activity of, e.g., alanine:glyoxalate aminotransferase, glyoxylate reductase/hydroxypyruvate reductase, hepatic glycolate oxidase, dihydrodipicolinate synthase, or another enzymes involved in oxalate metabolism or associated with hyperoxaluria. In other embodiments, methods for treating individuals having reduced or lacking *Oxalobacter formigenes* enteric colonization are provided. See e.g., Hoppe et al., *Kidney Int.* 70:1305-11 (2006); Hoppe et al., *Am. J. Kidney Dis.* 58:453-55(2011).

The disclosed methods may include treating a mammalian subject at risk for, susceptible to, or afflicted with a condition associated with elevated levels of oxalate. The populations treated by the methods of the present disclosure may include, but are not limited to, subjects suffering from, or at risk for developing an oxalate-associated disorder such as, e.g., oxalosis, hyperoxalemia, primary hyperoxaluria, or enteric hyperoxaluria.

Subjects treated according to the methods of the invention may include but are not limited to mammals, including humans, non-human primates, primates, baboons, chimpanzees, monkeys, rodents (e.g., mice, rats), rabbits, cats, dogs, horses, cows, sheep, goats, pigs, etc.

Many methods are available to assess development or progression of an oxalate-associated disorder or a condition associated with elevated oxalate levels. Such disorders may include, but are not limited to, any condition, disease, or disorder as defined above. Development or progression of an oxalate-associated disorder may be assessed by measurement of urinary oxalate, plasma oxalate, measurement of kidney or liver function, or detection of calcium oxalate deposits, for example.

A condition, disease, or disorder may be identified by detecting or measuring oxalate concentrations, for example in a urine sample or other biological sample or fluid. For example, hyperoxalemia may be identified by detecting or measuring oxalate concentrations in a blood sample. An early symptom of hyperoxaluria may include kidney stones due to, e.g., oxalosis, which may be associated with severe or sudden abdominal or flank pain, blood in the urine, frequent urges to urinate, pain when urinating, or fever and chills. Kidney stones may be symptomatic or asymptomatic, and may be visualized, for example by imaging the abdomen by x-ray, ultrasound, or computerized tomography (CT) scan. If hyperoxaluria is not controlled, the kidneys are damaged and kidney function is impaired. Kidneys may even fail.

Kidney failure (and poor kidney function) may be identified by a decrease in, or lacking urine output (reduced glomerular filtration rate), general ill feeling, tiredness, and marked fatigue, nausea, vomiting, anemia, and/or failure to develop and grow normally in young children.

Calcium oxalate deposits in other tissues and organs may also be detected by methods including direct visualization (e.g., in the eyes), x-ray, ultrasound, CT, echocardiogram, or biopsy (e.g., bone, liver, or kidney). Kidney and liver function, as well as oxalate concentrations, may also be assessed using art-recognized direct and indirect assays. The chemical content of urine, blood or other biological sample may also be tested by well-known techniques. For example, oxalate, glycolate, and glycerate levels may be measured. Assays for liver and kidney function are well known, such as, for example, the analysis of liver tissue for enzyme deficiencies and the analysis of kidney tissue for oxalate deposits. Samples may also be tested for DNA changes known to cause different types of primary hyperoxaluria.

Other indications for treatment may include, but are not limited to, the presence of one or more risk factors, including those discussed previously and in the following sections. A subject at risk for developing or susceptible to a condition, disease, or disorder or a subject who may be particularly receptive to treatment with the compositions described herein may be identified by ascertaining the presence or absence of one or more such risk factors, diagnostic, or prognostic indicators. Similarly, an individual at risk for developing an oxalate-associated disorder may be identified by analysis of one or more genetic or phenotypic markers.

In some embodiments, the methods disclosed may be useful in subjects with urinary oxalate levels of at least 30, 40, 50, 60, 70, 80, 90, 100, 110, 120, 130, 140, 150, 160, 170, 180, 190, 200, 210, 220, 230, 240, 250, 260, 270, 280, 290, or 300 mg of oxalate per 24 hour period, or more. In certain embodiments, the oxalate level may be associated with one or more symptoms or pathologies. Oxalate levels may be measured in a biological sample, such as a body fluid including, for example, blood, serum, plasma, or urine. Optionally, oxalate may be normalized to a standard protein or substance, such as creatinine in urine. In some embodiments, the methods may include administration of the compositions described herein to reduce circulating oxalate levels in a subject to undetectable levels, or to less than 1%, 2%, 5%, 10%, 15%, 20%, 25%, 30%, 35%, 40%, 45%. 50%, 55%, 60%, 65%, 70%, 75%, or 80% of the subject's oxalate levels prior to treatment.

Hyperoxalemia and/or oxalosis are often associated with different types of hyperoxaluria. Hyperoxaluria in humans can be characterized by urinary oxalate excretion of greater than 40 mg (approximately 440 µm). Exemplary clinical cutoff levels are 43 mg/day (approximately 475 µmol) for men and 32 mg/day (approximately 350 µmol) for women, for example. Hyperoxaluria can also be defined as urinary oxalate excretion greater than 30 mg per day per gram of urinary creatinine. Persons with mild hyperoxaluria may excrete about 30-60 (approximately 342-684 µmol) or about 40-60 (approximately 456-684 µmol) mg of oxalate per day. Persons with enteric hyperoxaluria may excrete about 45-80 mg (approximately 513-912 µm) of urinary oxalate per day, and persons with primary hyperoxaluria may excrete at least 80 mg (approximately 912 µm) per day, for example. Borowski ct al., *Exp. Opinion Pharmacother.* 7:1887-96 (2006); Hoppe, Nat. Rev. Nephrol. 8:467-75 (2012).

A method of treating a disorder associated with elevated metabolite, e.g., oxalate, concentration in a mammal is provided. The method may comprise administering the peritoneal solution comprising a metabolizing enzyme, such as, e.g., those described herein or a functional fragment thereof, to the mammal in a therapeutically effective amount. In some embodiments, the method may comprise preparing a peritoneal dialysis solution with at least one metabolizing enzyme or a functional fragment thereof, and administering the enzyme-supplemented peritoneal dialysis solution to the mammal in a therapeutically effective amount. In some embodiments, the peritoneal dialysis solution may be administered via a peritoneal dialysis apparatus, e.g., a catheter. In certain cases, the peritoneal dialysis solution is administered to reduce endogenous or exogenous metabolite levels and/or concentrations. In some embodiments, the peritoneal dialysis solution reduces metabolite levels and/or concentrations in the peritoneal cavity of the mammal. In some embodiments, the metabolite is oxalate. In other embodiments, the metabolite is chosen from uric acid, urea, bilirubin, and phenylalanine. In some embodiments, the disorder is chosen from hyperuricemia, gout, uremia, hyperbilirubinemia, jaundice, hyperphenylalaninemia, and phenylketonuria (PKU). In certain embodiments, the methods described herein can be combined with other methods of treating elevated metabolite concentration, such as, e.g., hemodialysis.

The metabolizing enzyme may be used to supplement a peritoneal dialysis solution as the sole active compound or in combination with another active compound or composition. The dosage of the enzyme and the duration of peritoneal dialysis may be selected based on the severity of the symptoms and the progression of the disease. The appropriate therapeutically effective dose of metabolizing enzymes can be selected by a treating clinician. Additionally, specific dosages indicated in the Examples or known in the art (e.g., Physicians' Desk Reference (PDR) 2003, 57th ed., Medical Economics Company. 2002) may be used.

In some embodiments, the dosage of the metabolizing enzyme may be about 50, about 100, about 150, or about 200 units, per 100 ml peritoneal dialysis solution. In some embodiments, the dosage may be about 150 units enzyme per 100 ml peritoneal dialysis solution. In some embodiments, the dosage of the metabolizing enzyme may be about 0.5, about 1.0, about 1.5, or about 2.0 g, per 100 ml peritoneal dialysis solution. In some embodiments the dosage may be about 1.5 g enzyme per 100 ml peritoneal dialysis solution. In some embodiments, about 10 nd, 20 ml, 30 ml, 40 ml, 50 ml, or 60 ml of peritoneal dialysis solution per kg body weight may be administered to a mammal, such as a human, per cycle. The duration of each cycle of peritoneal dialysis may range from about 2 to about 12 hours, such as, e.g., about 4 to about 12 hours, or about 2 to about 8 hours. In some embodiments, the duration of each cycle of peritoneal dialysis may range from about 4 to about 6 hours. Multiple cycles of peritoneal dialysis may be performed, for example, for up to several weeks or months.

Before, during, and after peritoneal dialysis, metabolite, e.g., oxalate, levels in the mammal may be measured in a biological sample, such as a body fluid including, for example, blood, serum, plasma, urine, or peritoneal fluid. Metabolite levels may be also measured in the peritoneal dialysis solution in circulation. In some embodiments, metabolite levels may be measured in other biological samples, such as a sample collected from a tissue, for example, the eye, bone marrow, kidney, liver, or heart, or a sample collected from the contents of one or more of the following: stomach, proximal small intestine, distal small intestine, cecum, colon, or rectum. Metabolite, e.g., oxalate, levels in the mammal may be reduced via the methods described herein, such as the methods of peritoneal dialysis described herein.

Animal Models

An animal model of hyperoxalemia and/or peritoneal dialysis is also provided. In some embodiments, the non-human animal model may comprise a mammal. In some embodiments, the mammal may be a pig. The animal may be administered with continuous infusion of oxalate. The administration can be conducted using methods known in the art. For example, the animal may be inserted with a first device for administering the continuous infusion of oxalate. In some embodiments, the first device may be chosen from a catheter and a pleural trocar. The catheter may be inserted percutaneously with or without surgery. In some embodiments, the catheter may be a peripheral venous catheter, such as VENFLON™ or CATHLON™. In some embodiments, an infusion pump may also be used. The oxalate concentration in the administered solution may be between about 0.1% and about 10% (w/w). In some embodiments, the oxalate concentration may be 1%. For example, the administered solution may comprise 1% sodium oxalate and 0.9% NaCl (saline). The rate, volume, and duration of infusion may be selected based on the desired oxalate levels in the blood of the animal. For example, the rate of infusion may be between about 0.05 and about 2 mL/min. In some embodiments, the rate of infusion may be between about 0.15 to about 0.40 mL/min, such as about 0.17 mL/min, 0.20 mL/min, 0.27 mL/min, or 0.35 mL/min. The volume of infusion may be between about 1 and about 8 mL/kg body weight. In some embodiments, the volume of infusion may be between about 3 and about 5 mL/kg body weight, such as about 4 mL/kg body weight. The duration of infusion may be between about 1 and about 72 hours. In some embodiments, the duration of infusion may be between about 4 and about 6 hours, such as 5 hours. In some embodiments, the infusion may be performed for up to several weeks. In some embodiments, bolus infusions may be performed without a pump. For example, the bolus infusions may be performed at a time interval. In some embodiments, the time interval may be every 10, 20, 30, 40, 50, or 60 minutes.

Before, during, and after the infusion or peritoneal dialysis, oxalate levels in the animal model may be measured in a biological sample, such as a body fluid including, for example, blood, serum, plasma, urine, or peritoneal fluid. Oxalate levels may be also measured in the peritoneal dialysis solution. In some embodiments, oxalate levels may be measured in other biological samples, such as a sample collected from a tissue, for example, the eye, bone marrow, kidney, liver, or heart, or a sample collected from the contents of one or more of the following: stomach, proximal small intestine, distal small intestine, cecum, colon, or rectum. Oxalate levels in the animal model may be reduced via the methods described herein, such as the methods of peritoneal dialysis described herein.

The following examples provide illustrative embodiments of the present disclosure. One of ordinary skill in the art will recognize the numerous modifications and variations that may be performed without altering the spirit or scope of the present disclosure. Such modifications and variations are encompassed within the scope of the present disclosure. The Examples do not in any way limit the present disclosure. The contents of all the patent and non-patent literature documents cited in the present disclosure are incorporated by reference in their entireties.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Animal Handling and Surgery

The study was performed in pigs (n=4–6) weighing approximately 20±2 kg each. Animals were maintained on a 12-hour day-night cycle, with light from 06.00-18.00 (6 am-6 pm) and dark from 18.00-06.00 (6 pm-6 am) hours. The pigs were individually housed in pens equipped with a dry feeding trough, a drinking nipple and a constant heating lamp (150 W). They were allowed to move freely within their pen and had visual contact with each other when not in the experiment.

The pigs were fasted overnight and then pre-medicated with azaperone (Stresnil, Janssen Pharmaceutical, Belgium, 4.0 mg/kg 1M) before transport and further handling. At surgery pigs were anesthetized with isoflurane (Forene 100%, Abbot Scandinavia AB, Solna, Sweden) mixed with 2% air and supplemented with medical oxygen (0.5 L/min) using a closed-circuit system (Komesaroff Medical Developments, Melbourne, Australia).

The pig's external right jugular vein was catheterized with two catheters (Standards Silicone Tubing, Helix Medical Carpinteria, Calif., USA). One catheter for blood sampling was inserted, 6 cm deep, and another for continuous infusion of sodium oxalate, 8 cm deep, and both catheters size: 30 cm long (I.D. 1.02 mm and O.D. 2.16 mm). Catheter was inserted from 4 cm long incision on the neck between bronchial join and mandibular axis.

A health record was kept for each animal from the entry in the study. It was the basis for any subsequent exclusion. All pigs were fed cereal-based feed for young growing pigs (53908 VAXTILL 320 P BK, Lantmannen, Sweden), twice daily (2% body mass per meal). This amount was comparable to the amount of consumed food when given ad libitum in similar conditions.

To perform peritoneal dialysis (PD), a tube 30 cm long, perforated at the end and on 2-3 places within 30 cm of the tube length (id 3.8 mm and od 4.4 mm), was inserted into the abdominal cavity through the 1 cm wide, skin and muscle-splitting incision. To close the skin "hole." the grommet incision was sutured to the surrounding tissues for further stabilization of the catheter. PD solution, based on the pig body weight (20-40 mL/kg), was infused within 5 min and the same tube was used to drain solute out.

Example 2

Establishment of Porcine Model of Hyperoxalemia aud PD

Pigs under total anesthesia with isoflurane were infused with sodium oxalate as 1% solution (1% sodium oxalate in 0.9% NaCl (saline), Sigma-Aldrich Chemicals; or the amount oxalate was 1% (w/w) of total daily food intake, e.g., 10 g oxalate per 1 kg total daily food intake) continuously through a jugular vein at a constant rate of 0.20 or 0.35 mL/min with an infusion pump (KD Scientific Syringe Pump Legato 100, KD Scientific Inc. Holliston, Mass., USA). To titer the plasma oxalate levels between 100-200 $\mu$mol/L, infusion was carried out at a rate of 0.20 or 0.35 mL/min, during 4-6 h of infusion. PD started at the same time as oxalate infusion with a PD volume of 40 mL/kg of pig body weight. For a 20 kg pig having 2 L blood volume. 800 mL PD solution (GAMBROSOL TRIO™ 10, glucose H 3.9%, pH 6.3) was administered. The pH of PD was 7.4, at 5-10 min after start of PD. As shown in FIGS. 1a and 1b, the infusion rate of 0.2 mL/min and 0.35 mL/min produced hyperoxalemia at about 60-100 $\mu$m/L and about 120-180 $\mu$mol/L during 4 h, respectively. The average infusion period was about 4 hours.

Blood samples were collected at 30 min time points during infusion and peritoneal dialysis, and just before the start of infusion for baseline measurement. Each blood sample was transferred immediately to tubes for plasma and/or serum collection, and kept on ice until centrifuged at 4° C. The collected samples were stored at −20° C. until further analysis for oxalate estimation using ion chromatography. Serum samples were diluted ⅒ with Millipore water and filtered using centrifugal filters with molecular weight cut off (MWCO) 3 kDa (VWR International). 0.5 mL of filtrate was transferred to PP vials and placed in autosampler for analysis on the ICS-900 (Thermo Scientific).

GAMBROSOL TRIO™ 10 (Gambro AB, Lund, Sweden) was used as dialysate of the PD. 1.5 g (65 units) of powdered OXDC (Oxalate decarboxylase from *Bacillus subtilis*, spray dry crystalline, Lot: 44#3, activity per total dry weight 10.9 u/mg at optimal pH 4) was mixed in 100 mL of PD prior to injection into peritoneal cavity that was already filled with PD (40 mL/kg of body weight). In negative controls, only GAMBROSOL TRIO™ 10 was infused.

PD samples were collected every 30 minutes, parallel with blood samples. The collected samples were stored at −20° C. until further analysis. PD samples were diluted ⅒ with Millipore water and filtered using centrifugal filters with molecular weight cut off (MWCO) 3 kDa (VWR International). 0.5 mL of filtrate was transferred to PP vials and placed in autosampler for analysis using ion chromatography (ICS-900). At the end of the experiment, the peritoneal cavity was drained and the volume of collected dialysate was recorded.

The pigs were re-used several times. At the end of the last experiment, the pigs were sacrificed with an overdose of pentobarbital (Allfatal vet. Omnidea AB, Sweden). Chyme samples from the stomach, proximal small intestine, distal small intestine, cecum, colon and rectum were collected and volume recorded. Samples were kept at −20° C. until analyzed for oxalate content.

To measure oxalate content chyme samples were weighed then mixed with 9 volumes of 240 mM HCl and incubated 1 hour at 60° C. to ensure complete solubilization of oxalate crystals. After that, samples were diluted 1/100 with 0.4 M boric acid, then centrifuged using centrifugal filters with molecular weight cut off (MWCO) 3 kDa (VWR International) at 14000 g for 30 min. 0.5 mL of filtrate was transferred to PP vials and placed in autosampler of ion chromatography (ICS-900) for oxalate measurement. Samples were kept at −20° C. until analyzed for oxalate content.

Oxalate concentration in samples was analyzed using an ion chromatography (IC) method with an ICS-900 with AS-DV autosampler (both Thermo Scientific). The ICS-900 was equipped with IonPack AG4A-SC (2×50 mm) guard column, IonPack AS4A-SC (2×250 mm) analytical column, Anion Micro Membrane Suppressor (AMMS 300) in Displacement Chemical Regeneration Mode (DCR), and 10 $\mu$L sample loop (all from Thermo Scientific). The mobile phase was 1.8 mM $Na_2CO_3$/1.7 mM $NaHCO_3$ at flow rate 0.5 mL/min. Regenerant for AMMS 300 was 75 mN $H_2SO_4$. Statistical analysis was performed using Student t-test or ANOVA or Prism 6 Graph. Differences were considered significant if $p<0.05$.

Pigs were infused with a constant rate of sodium oxalate (0.17 mL/min, 1% sodium oxalate in 0.9% sodium chloride)

for 6 h. 1.5 g powder crystalline OXDC was mixed with GAMBROSOL TRIO™ 10 before PD dialysis. PD+1.5 g OXDC (about 65 U) was started at the same time as the start of oxalate infusion at 40 mL/kg body weight (about 2 L blood/800 mL PD).

TABLE 1

|  | Sample | AUC | P < 0.05 (paired t-test) |
| --- | --- | --- | --- |
| Control | Serum | 275.0 ± 13.9 |  |
|  | PD | 74.9 ± 3 |  |
| OXDC | Serum | 229.2 ± 9.2 | 0.014 |
|  | PD | 57.3 ± 4.4 | 0.035 |

Statistical analysis was performed using or ANOVA, student paired t-test Prism 6 Graph. Differences were considered significant if p<0.05.

Peritoneal dialysis with OXDC that was started at the same time as oxalate infusion was able to remove from circulation on average about 20-40% of total serum oxalate. Similar to results in humans with traditional PD, the degree of removal depended on the plasma levels of oxalate and the duration of dialysis, see e.g., Illies et al., *Kidney Int.* 70:1642-48 (2006)). The results in this experiment (FIG. 2 and Table 1) showed that OXDC degraded oxalate in biological fluids such as serum and PD from hyperoxalemic pigs. Oxalate concentration in these biological fluids was dependent on OXDC activity.

Example 3

Development of In Vitro PD System

Samples from in vitro studies shown in FIGS. 3 and 5 were collected and stored at −20° C. until further analyzed for oxalate estimation using the IC method as described above. Statistical analysis was performed using Student t-test or ANOVA or Prism 6 Graph. Differences were considered significant if p<0.05.

As shown in FIG. 3, dialysis was performed using a beaker containing 50 mM TrisCL pH 7.4 that mimicked the blood compartment and a dialysis bag that mimicked the peritoneal cavity filled with dialysis solution and was placed in the beaker with a final concentration of oxalate of 100 μmol/L. The dialysis bag (10 kDa pores, Fisher) contained GAMBROSOL TRIO™ 10 (Gambro, Renal Products, Lund. Sweden), glucose High ±1.5 g crystalline OXDC (about 15 mg/mL, or total of about 64 units of OXDC at pH 7.4) (TrisCL GAMBROSOL TRIO™ 10 ratio=2.5:1, similar to the ratio in dialysis performed in humans). pH in the bag was 7.0 after 5 min of dialysis. Samples were taken from the bag and the beaker at 0 min, 30 min, 60 min, 240 min and overnight for oxalate measurement (FIG. 4).

As shown in FIG. 5, dialysis was performed using a beaker containing pig serum spiked with sodium oxalate at a final concentration of 100 μmol/L (mimicking serum from pigs with hyperoxalemia) and a dialysis bag (10 kDa pores, Fisher) containing GAMBROSOL TRIO™ 10 (Gambro, Renal Products, Lund. Sweden), glucose H ±70 mg of crystalline OXDC (about 30 mg/mL, or total of about 3 units of OXDC at pH 7.4) (Serum: GAMBROSOL TRIO™ 10 ratio=2.5:1, similar to the ratio in dialysis performed in humans). Samples were taken from the bag and the beaker at 0 min, 30 min, 60 min, 240 min and overnight for oxalate measurement. The results shown in FIG. 6 demonstrated that oxalate level in the bag with GAMBROSOL TRIO™ 10±OXDC (representing "peritoneal dialysate") was reduced to about 17.4% of the total basal serum oxalate after 1 h of dialysis and stayed in that range until the end of dialysis at 6 h.

To determine the minimal dose of OXDC that can significantly reduce serum oxalate levels, the in vitro study described above was performed with different concentrations of OXDC in GAMBROSOL TRIO™ 10 (about 30, 20, 15, 10, 5 and 1 mg/mL) and a starting oxalate serum concentration of 100 μmol/L (serum spiked with sodium oxalate as described above) at a constant shaking speed of 130 rpm at 37° C. for up to 6 h. Samples were taken from the beaker at 0 min, 30 min, 60 min, 240 and 360 min for oxalate measurement.

The results shown in FIG. 7 demonstrated that serum oxalate levels were reduced 35% with 10 mg/mL of OXDC after 6 h incubation. Thus, at pH 7.4 (pH of serum and biological fluids) OXDC used in the experiment had a potency of less than 0.1 units/mg substrate.

What is claimed is:

1. A method of treating hyperoxaluria and/or hyperoxalemia by peritoneal dialysis in a subject in need thereof, the method comprising administering into the peritoneal cavity of the subject a peritoneal dialysis solution comprising oxalate decarboxylase enzyme or a functional fragment thereof.

2. The method of claim 1, wherein the method is combined with hemodialysis.

3. The method of claim 1, wherein the oxalate decarboxylase is covalently modified.

4. The method of claim 3, wherein the oxalate decarboxylase is PEGylated.

5. The method of claim 1, wherein the oxalate decarboxylase is crystallized.

6. The method of claim 1, wherein the oxalate decarboxylase is uncrosslinked.

7. The method of claim 1, wherein the oxalate decarboxylase is crosslinked.

8. The method of claim 1, wherein the peritoneal dialysis solution comprises at least one osmotic agent, at least one electrolyte, and at least one organic acid salt.

9. The method of claim 1, wherein the subject is a human subject.

\* \* \* \* \*